United States Patent
Reichgott et al.

(10) Patent No.: US 11,426,105 B2
(45) Date of Patent: *Aug. 30, 2022

(54) FLOWOMETRY IN OPTICAL COHERENCE TOMOGRAPHY FOR ANALYTE LEVEL ESTIMATION

(71) Applicant: Masimo Corporation, Irvine, CA (US)

(72) Inventors: Samuel Reichgott, Coopersburg, PA (US); Walter J. Shakespeare, Macungie, PA (US); George Kechter, Peoria, IL (US); Phillip William Wallace, Bernardsville, NJ (US); Matthew J. Schurman, Richboro, PA (US)

(73) Assignee: Masimo Corporation, Irvine, CA (US)

( * ) Notice: Subject to any disclaimer, the term of this patent is extended or adjusted under 35 U.S.C. 154(b) by 716 days.

This patent is subject to a terminal disclaimer.

(21) Appl. No.: 16/444,960

(22) Filed: Jun. 18, 2019

(65) Prior Publication Data
US 2019/0357823 A1 Nov. 28, 2019

Related U.S. Application Data

(63) Continuation of application No. 14/711,610, filed on May 13, 2015, now Pat. No. 10,368,787, which is a
(Continued)

(51) Int. Cl.
*A61B 5/1455* (2006.01)
*A61B 5/00* (2006.01)
(Continued)

(52) U.S. Cl.
CPC ........ *A61B 5/14551* (2013.01); *A61B 5/0066* (2013.01); *A61B 5/0073* (2013.01);
(Continued)

(58) Field of Classification Search
CPC ..... A61B 5/026; A61B 5/0261; A61B 5/1455; A61B 5/14551; A61B 5/14552;
(Continued)

(56) References Cited

U.S. PATENT DOCUMENTS 3,826,905 A 7/1974 Valkama et al.
3,958,560 A 5/1976 March
(Continued)

FOREIGN PATENT DOCUMENTS

EP 0282234 9/1988
EP 0160768 5/1989
(Continued)

OTHER PUBLICATIONS

U.S. Pat. No. 7,254,429, Method and Apparatus for Monitoring Glucose Levels in a Biological Tissue, Aug. 7, 2007.
(Continued)

*Primary Examiner* — Chu Chuan Liu
(74) *Attorney, Agent, or Firm* — Knobbe Martens Olson & Bear LLP

(57) ABSTRACT

Optical coherence tomography (herein "OCT") based analyte monitoring systems are disclosed. In one aspect, techniques are disclosed that can identify fluid flow in vivo (e.g., blood flow), which can act as a metric for gauging the extent of blood perfusion in tissue. For instance, if OCT is to be used to estimate the level of an analyte (e.g., glucose) in tissue, a measure of the extent of blood flow can potentially indicate the presence of an analyte correlating region, which would be suitable for analyte level estimation with OCT. Another aspect is related to systems and methods for scanning multiple regions. An optical beam is moved across the surface of the tissue in two distinct manners. The first can be a coarse scan, moving the beam to provide distinct scanning
(Continued)

positions on the skin. The second can be a fine scan where the beam is applied for more detailed analysis.

20 Claims, 16 Drawing Sheets

Related U.S. Application Data continuation of application No. 14/063,977, filed on Oct. 25, 2013, now Pat. No. 9,060,721, which is a continuation of application No. 12/397,593, filed on Mar. 4, 2009, now Pat. No. 8,571,617.

(60) Provisional application No. 61/033,584, filed on Mar. 4, 2008, provisional application No. 61/068,058, filed on Mar. 4, 2008.

(51) Int. Cl.
*A61B 5/026* (2006.01)
*A61B 5/145* (2006.01)

(52) U.S. Cl.
CPC ............ *A61B 5/026* (2013.01); *A61B 5/0261* (2013.01); *A61B 5/1455* (2013.01); *A61B 5/14532* (2013.01); *A61B 5/14546* (2013.01); *A61B 5/4875* (2013.01); *A61B 5/725* (2013.01); *A61B 5/7221* (2013.01); *A61B 5/7278* (2013.01); *A61B 2576/00* (2013.01)

(58) Field of Classification Search
CPC ............ A61B 5/14546; A61B 5/14532; A61B 5/7221; A61B 5/7278; A61B 5/725; A61B 5/4875; A61B 5/0066; A61B 5/0073
See application file for complete search history.

(56) References Cited

U.S. PATENT DOCUMENTS

| | | |
|---|---|---|
| 4,014,321 A | 3/1977 | March |
| 4,476,875 A | 10/1984 | Nilsson et al. |
| 4,590,948 A | 5/1986 | Nilsson |
| 4,606,351 A | 8/1986 | Lubbers |
| 4,655,225 A | 4/1987 | Dahne et al. |
| 4,704,029 A | 11/1987 | Van Heuvelen |
| 4,731,363 A | 3/1988 | Hamilton et al. |
| 4,743,604 A | 5/1988 | Alig et al. |
| 4,746,211 A | 5/1988 | Ruth et al. |
| 4,750,830 A | 6/1988 | Lee |
| 4,834,111 A | 5/1989 | Khanna et al. |
| 4,871,755 A | 10/1989 | Alig et al. |
| 4,873,989 A | 10/1989 | Einzig |
| 4,882,492 A | 11/1989 | Schlager |
| 4,883,953 A | 11/1989 | Koashi et al. |
| 4,890,621 A | 1/1990 | Hakky et al. |
| 4,901,728 A | 2/1990 | Hutchinson |
| 4,948,248 A | 8/1990 | Lehman |
| 4,960,128 A | 10/1990 | Gordon et al. |
| 4,964,408 A | 10/1990 | Hink et al. |
| 4,979,509 A | 12/1990 | Hakky |
| 4,989,978 A | 2/1991 | Groner |
| 5,025,785 A | 6/1991 | Weiss |
| 5,028,787 A | 7/1991 | Rosenthal et al. |
| 5,041,187 A | 8/1991 | Hink et al. |
| 5,054,487 A | 10/1991 | Clarke |
| 5,069,213 A | 12/1991 | Polczynski |
| 5,070,874 A | 12/1991 | Barnes et al. |
| 5,101,814 A | 4/1992 | Palti |
| 5,112,124 A | 5/1992 | Harjunmaa et al. |
| 5,115,133 A | 5/1992 | Knudson |
| 5,163,438 A | 11/1992 | Gordon et al. |
| 5,168,325 A | 12/1992 | Yoder-Short |
| 5,178,153 A | 1/1993 | Einzig |
| 5,209,231 A | 5/1993 | Cote et al. |
| 5,222,495 A | 6/1993 | Clarke et al. |
| 5,222,496 A | 6/1993 | Clarke et al. |
| 5,243,983 A | 9/1993 | Tarr et al. |
| 5,267,152 A | 11/1993 | Yang et al. |
| 5,277,181 A | 1/1994 | Mendelson et al. |
| 5,278,627 A | 1/1994 | Aoyagi et al. |
| 5,313,941 A | 5/1994 | Braig et al. |
| 5,319,355 A | 6/1994 | Russek |
| 5,321,501 A | 6/1994 | Swanson et al. |
| 5,337,744 A | 8/1994 | Branigan |
| 5,341,805 A | 8/1994 | Stavridi et al. |
| 5,348,003 A | 9/1994 | Caro |
| 5,349,953 A | 9/1994 | McCarthy et al. |
| 5,361,758 A | 11/1994 | Hall et al. |
| D353,195 S | 12/1994 | Savage et al. |
| D353,196 S | 12/1994 | Savage et al. |
| 5,370,114 A | 12/1994 | Wong et al. |
| 5,372,136 A | 12/1994 | Steuer et al. |
| 5,376,336 A | 12/1994 | Lubbers et al. |
| 5,377,676 A | 1/1995 | Vari et al. |
| 5,379,238 A | 1/1995 | Stark |
| 5,383,452 A | 1/1995 | Buchert |
| 5,398,681 A | 3/1995 | Kupershmidt |
| D359,546 S | 6/1995 | Savage et al. |
| 5,431,170 A | 7/1995 | Mathews |
| 5,433,197 A | 7/1995 | Stark |
| 5,435,309 A | 7/1995 | Thomas et al. |
| D361,840 S | 8/1995 | Savage et al. |
| D362,063 S | 9/1995 | Savage et al. |
| 5,448,992 A | 9/1995 | Kupershmidt |
| 5,452,716 A | 9/1995 | Clift |
| 5,452,717 A | 9/1995 | Branigan et al. |
| D363,120 S | 10/1995 | Savage et al. |
| 5,456,252 A | 10/1995 | Vari et al. |
| 5,457,535 A | 10/1995 | Schmidtke et al. |
| 5,459,570 A | 10/1995 | Swanson et al. |
| 5,479,934 A | 1/1996 | Imran |
| 5,482,036 A | 1/1996 | Diab et al. |
| 5,490,505 A | 2/1996 | Diab et al. |
| 5,492,118 A | 2/1996 | Gratton et al. |
| 5,494,043 A | 2/1996 | O'Sullivan et al. |
| 5,501,226 A | 3/1996 | Petersen et al. |
| 5,533,511 A | 7/1996 | Kaspari et al. |
| 5,534,851 A | 7/1996 | Russek |
| 5,535,743 A | 7/1996 | Backhaus et al. |
| 5,549,114 A | 8/1996 | Petersen et al. |
| 5,551,422 A | 9/1996 | Simonsen et al. |
| 5,553,616 A | 9/1996 | Ham et al. |
| 5,561,275 A | 10/1996 | Savage et al. |
| 5,562,002 A | 10/1996 | Lalin |
| 5,582,168 A | 12/1996 | Samuels et al. |
| 5,582,171 A | 12/1996 | Chornenky et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| 5,710,630 A | 1/1998 | Essenpreis et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,795,295 A | 8/1998 | Hellmuth et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |

(56) References Cited

U.S. PATENT DOCUMENTS

| | | |
|---|---|---|
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,036,919 A | 3/2000 | Thym et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,147,108 A | 11/2000 | Hauptman |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,173,197 B1 | 1/2001 | Boggett et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,294,062 B1 | 9/2001 | Bruck, Jr. et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,425,863 B1 | 7/2002 | Werner et al. |
| 6,430,437 B1 | 8/2002 | Marro |
| 6,430,525 B1 | 8/2002 | Weber et al. |
| 6,443,881 B1 | 9/2002 | Finger |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,216 B1 | 4/2003 | Wilsey et al. |
| 6,541,756 B2 | 4/2003 | Schulz et al. |
| 6,542,764 B1 | 4/2003 | Al-Ali et al. |
| 6,544,212 B2 | 4/2003 | Galley et al. |
| 6,549,801 B1 * | 4/2003 | Chen ............... A61B 5/0261 600/473 |
| 6,556,853 B1 | 4/2003 | Cabib et al. |
| 6,572,566 B2 | 6/2003 | Effenhauser |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,707,554 B1 | 3/2004 | Miltner et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,073 B1 | 4/2004 | Motamedi et al. |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,780,651 B2 | 8/2004 | Douglas et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,836,337 B2 | 12/2004 | Cornsweet |
| 6,837,337 B2 | 1/2005 | Thomas et al. |
| 6,847,449 B2 | 1/2005 | Bashkansky et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,020,506 B2 | 3/2006 | Fine et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |

(56) References Cited

U.S. PATENT DOCUMENTS

| | | |
|---|---|---|
| 7,190,261 B2 | 3/2007 | Al-Ali |
| 7,190,464 B2 | 3/2007 | Alphonse |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,280,860 B2 | 10/2007 | Ikeda et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,307,734 B2 | 12/2007 | Dogariu |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,353,055 B2 | 4/2008 | Hogan |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,557,929 B2 | 7/2009 | Fang-Yen et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,884,945 B2 | 2/2011 | Srinivasan et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,168 B2 | 7/2012 | Lowery |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |

(56) References Cited

U.S. PATENT DOCUMENTS

| | | | |
|---|---|---|---|
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |

(56) References Cited

U.S. PATENT DOCUMENTS

| | | |
|---|---|---|
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |

(56) References Cited

U.S. PATENT DOCUMENTS

| | | |
|---|---|---|
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| D833,624 S | 11/2018 | DeJong et al. |
| 10,123,726 B2 | 11/2018 | Al-Ali et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 2002/0016533 A1 | 2/2002 | Marchitto et al. |
| 2004/0162471 A1 | 8/2004 | Ikeda et al. |
| 2004/0167382 A1 | 8/2004 | Gardner et al. |
| 2004/0260158 A1 | 12/2004 | Hogan |
| 2004/0260183 A1* | 12/2004 | Lambert ............ A61B 3/102 600/476 |
| 2005/0043597 A1 | 2/2005 | Xie |
| 2005/0070771 A1 | 3/2005 | Rule et al. |
| 2005/0101846 A1 | 5/2005 | Fine et al. |
| 2005/0105097 A1 | 5/2005 | Fang-Yen et al. |
| 2005/0226912 A1 | 10/2005 | Lowery |
| 2005/0254061 A1 | 11/2005 | Alphonse |
| 2006/0063988 A1 | 3/2006 | Schurman et al. |
| 2006/0161054 A1 | 7/2006 | Reuss et al. |
| 2006/0187462 A1 | 8/2006 | Srinivasan |
| 2006/0264719 A1 | 11/2006 | Schurman et al. |
| 2006/0276696 A1 | 12/2006 | Schurman et al. |
| 2007/0249917 A1 | 10/2007 | Ballerstadt et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2011/0082711 A1 | 4/2011 | Poeze et al. |
| 2011/0125060 A1 | 5/2011 | Telfort et al. |
| 2011/0208015 A1 | 8/2011 | Welch et al. |
| 2011/0230733 A1 | 9/2011 | Al-Ali |
| 2012/0165629 A1 | 6/2012 | Merritt et al. |
| 2012/0209084 A1 | 8/2012 | Olsen et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0296672 A1 | 11/2013 | O'Neil et al. |
| 2013/0324808 A1 | 12/2013 | Al-Ali et al. |
| 2013/0331660 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0257689 A1 | 9/2015 | Al-Ali et al. |
| 2015/0351697 A1 | 12/2015 | Weber et al. |
| 2015/0366507 A1 | 12/2015 | Blank |
| 2016/0029932 A1 | 2/2016 | Al-Ali |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0103598 A1 | 4/2016 | Al-Ali et al. |
| 2016/0196388 A1 | 7/2016 | Lamego |
| 2016/0197436 A1 | 7/2016 | Barker et al. |
| 2016/0213281 A1 | 7/2016 | Eckerbom et al. |

(56) References Cited

U.S. PATENT DOCUMENTS

| | | |
|---|---|---|
| 2016/0228043 A1 | 8/2016 | O'Neil et al. |
| 2016/0270735 A1 | 9/2016 | Diab et al. |
| 2016/0283665 A1 | 9/2016 | Sampath et al. |
| 2016/0287786 A1 | 10/2016 | Kiani |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0367173 A1 | 12/2016 | Dalvi et al. |
| 2017/0000394 A1 | 1/2017 | Al-Ali et al. |
| 2017/0014083 A1 | 1/2017 | Diab et al. |
| 2017/0024748 A1 | 1/2017 | Haider |
| 2017/0042488 A1 | 2/2017 | Muhsin |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0196464 A1 | 7/2017 | Jansen et al. |
| 2017/0196470 A1 | 7/2017 | Lamego et al. |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0311891 A1 | 11/2017 | Kiani et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0132769 A1 | 5/2018 | Weber et al. |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0253947 A1 | 9/2018 | Muhsin et al. |
| 2018/0256087 A1 | 9/2018 | Al-Ali et al. |
| 2018/0285094 A1 | 10/2018 | Housel et al. |
| 2018/0289325 A1 | 10/2018 | Poeze et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090760 A1 | 3/2019 | Kinast et al. |
| 2019/0090764 A1 | 3/2019 | Al-Ali |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |

FOREIGN PATENT DOCUMENTS

| | | |
|---|---|---|
| EP | 0127947 | 8/1990 |
| EP | 0280986 | 9/1992 |
| EP | 0317121 | 2/1994 |
| EP | 0536187 | 9/1994 |
| EP | 0589191 | 3/1997 |
| EP | 0603658 | 2/1999 |
| EP | 0631137 | 3/2002 |
| EP | 0670143 | 5/2003 |
| WO | WO 88/06726 | 9/1988 |
| WO | WO 89/10087 | 11/1989 |
| WO | WO 91/18548 | 12/1991 |
| WO | WO 92/10131 | 6/1992 |
| WO | WO 92/17765 | 10/1992 |
| WO | WO 93/00855 | 1/1993 |
| WO | WO 93/07801 | 4/1993 |
| WO | WO 93/09421 | 5/1993 |
| WO | WO 93/16629 | 9/1993 |
| WO | WO 94/04070 | 3/1994 |
| WO | WO 94/13193 | 6/1994 |

(56) References Cited

FOREIGN PATENT DOCUMENTS

| WO | WO 95/32416 | 11/1995 |
|---|---|---|
| WO | WO 02/65090 | 8/2002 |

OTHER PUBLICATIONS

U.S. Pat. No. 8,204,566, Method and Apparatus for Monitoring Blood Constituent Levels in Biological Tissue, Jun. 19, 2012.
U.S. Pat. No. 8,788,003, Monitoring Blood Constituent Levels in Biological Tissue, Jul. 22, 2014.
U.S. Pat. No. 7,822,452, Method for Data Reduction and Calibration of an OCT-Based Physiological Monitor, Oct. 26, 2010.
U.S. Pat. No. 8,306,596, Method for Data Reduction and Calibration of an OCT-Based Physiological Monitor, Nov. 6, 2012.
U.S. Pat. No. 9,078,560, Method for Data Reduction and Calibration of an OCT-Based Physiological Monitor, Jul. 14, 2015.
U.S. Pat. No. 9,668,679, Method for Data Reduction and Calibration of an OCT-Based Physiological Monitor, Jun. 6, 2017.
U.S. Pat. No. 10,130,291, Method for Data Reduction and Calibration of an OCT-Based Physiological Monitor, Nov. 20, 2018.
U.S. Pat. No. 8,036,727, Methods for Noninvasively Measuring Analyte Levels in a Subject, Oct. 11, 2011.
U.S. Pat. No. 8,548,549, Methods for Noninvasively Measuring Analyte Levels in a Subject, Oct. 1, 2013.
U.S. Pat. No. 9,554,737, Noninvasively Measuring Analyte Levels in a Subject, Jan. 31, 2017.
U.S. Pat. No. 8,768,423, Multispot Monitoring for Use in Optical Coherence Tomography, Jul. 1, 2014.
U.S. Pat. No. 9,833,180, Multispot Monitoring for Use in Optical Coherence Tomography, Dec. 5, 2017.
U.S. Pat. No. 8,571,617, Flowometry in Optical Coherence, Oct. 29, 2013.
U.S. Pat. No. 9,060,721, Flowometry in Optical Coherence, Jun. 23, 2015.
U.S. Pat. No. 10,368,787, Flowometry in Optical Coherence, Aug. 6, 2019.
U.S. Appl. No. 16/151,917, Method for Data Reduction and Calibration of an OCT-Based Physiological Monitor, filed Oct. 4, 2018.
U.S. Appl. No. 15/799,689, Multispot Monitoring for Use in Optical Coherence Tomography, filed Oct. 31, 2017.
Arnold, V.W. et al., "Fourier Transformation Infrared Spectrometry—A New (Old) Method of Detection in Forensic Chemistry and Criminal Investigation," Beitr Gerichtl Med. 47:123-47 (1989).
Arnold. M.A. et al., "Determination of Physiological Levels of Glucose in an Agueous Matrix with Digitally Filtered Fourier Transform Near-Infrared Spectra," Anal. Chem. 64(14):1457-64 (1990).
Bruulsema, J.T. et al., "Correlation Between Blood Glucose Concentration in Diabetics and Noninvasively Measured Tissue Optical Scattering Coefficient," Opt. Lett. 22(3):190-93 (1997).
Burritt, M.F., "Current Analytical Approaches to Measuring Blood Analytes," Clin. Chem. 36(8 pt.2):1562-66 (1990).
Chira, I.S. et al., "Light Scattering by Blood Components After Supplying Glucose," Biomed. Tech. 35(5):102-06 (1990).
Christison, G.B. et al., "Laser Photoacoustic Determination of Physiological Glucose Concentrations in Human Whole Blood," Med. Biol. Eng. Comput. 31(3):284-90 (1993).
Cote, G.L. et al., "Noninvasive Optical Polarimetric Glucose Sensing Using a True Phase Measurement Technigue," IEEE Trans. Biomed. Eng, 39(7):752-56 (1992).
CRC Press, "Handbook of Chemistry and Physics" 64th ed. pp. D-223, D-224, and D. 235.
Drezek, R. et al., "Light Scattering From Cell: Finite Difference Time-Domain Simulations and Goniometric Measurements," Appl. Opt. 38(16):3651-61 (1999).
Duck, F. A., Physical Properties of Tissue, (Academic London 1990).

Dyer, D.G et al., "Accumulation of Maillard Reaction Products in Skin Collagen in Diabetes and Aging," J. Clin. Invest. 91:2463-69 (1993).
Esenaliev, R.O, et al., "Noninvasive Monitoring of Glucose Concentration with Optical Coherence Tomography," Optics Lett. 26(13):992-94 (2001).
Faber, D.J. et al., "Light Absorption of (oxy-)Hemoglobin Assessed by Spectroscopic Optical Coherence Tomography," Optics Lett. 28(16):1436-38 (2003).
Fercher, A. et al., "In Vivo Optical Coherence Tomography," Amer, J. Ophthalmol, 116(1):113-14 (1993).
Flock, S.T. et al., "Total Attenuation Coefficients and Scattering Phase Functions of Tissues and Phantom Materials at 633 nm," Med. Phys. 14(5):835-41 (1987).
Fogt, E.J., "Continuous Ex Vivo and In Vivo Monitoring with Chemical Sensors," Clin. Chem. 36(8 pt.2):1573-80 (1990).
Frank, K.H et al., "Measurements of Angular Distributions of Rayleigh and Mie Scattering Events in Biological Models," Phvs. Med. Biol. 34(8):1901-16 (1989).
Gabriely.I. et al., "Transcutaneous Glucose Measurement Using Near-Infrared Spectroscopy During Hypoglycemia," Diabetes Care 22(12):2026-32 (1999).
Galanzha, E.I. et al., "Skin Backreflectance and Microvascular System Functioning at the Action of Osmotic Agents," J, Phys. D. Appl. Phys. 36:1739-46 (2003).
Gilbert, J.W. et al., "A Cerebrospinal Fluid Glucose Biosensor for Diabetes Mellitus," ASAIO J. 38(2):82-87 (1992).
Goetz, M.J. et al., "Application of a Multivariate Technique to Raman Spectra for Quantification of Body Chemicals," IEEE Trans, Biomed. Eng, 42:728-31 (1995).
Goodman, J.W., Some Fundamental Properties of Speckle, J. Optical Soc. of America 66(11):1145-50 (1976).
Gough, D.A., "The Composition and Optical Rotary Dispersion of Bovine Aqueous Humor," Diabetes Care 5(3):266-70 (1982).
Gunby, P., "Laser-Implant Contact Lens Could be Glucose Monitor," JAMA 243(4):317 (1980).
Guyton, A.C., Textbook of medical physiology, (W.B. Saunders Company 1992).
Huang, D, et al., "Optical Coherence Tomograph," Science 254:1178-81 (1991).
Huang, Y.L. et al., "On-Line Determination of Glucose Concentration Throughout Animal Cell Cultures Based on Chemiluminescent Detection of Hydrogen Peroxide Coupled with Flow-Injection Analysis," J. Biotechnol. 18(1-2):161-72 (1991).
International Search Report from PCT/US05/26744, dated Oct. 25, 2006.
International Search Report, from corresponding PCT/US06/13775, dated Sep. 13, 2006.
International Search Report, from corresponding PCT/US06/21535, dated Feb. 21, 2008.
Kaiser, N., "Laser Absorption Spectroscopy with an ATR Prism—Noninvasive in Vivo Determination of Glucose," Horm. Metab. Res. Suppl. 8:30-33 (1979).
Kajiwara, K. et al., "Spectroscopic Quantitative Analysis of Blood Glucose by Fourier Transform Infrared Spectroscopy with an Attenuated Total Reflection Prism," Med, Prog. Technol. 18(3):181-89 (1992).
Khalil, O.S. "Spectroscopic and Clinical Aspects of Noninvasive Glucose Measurements," Clin. Chem. 45(2):165-77 (1999).
Kholodnykh, A.I. et al., "Precision of Measurement of Tissue Optical Properties with Optical Coherence Tomography," Appl. Optics 42(16):3027-37 (2003).
King, T.W. et al., "Multispectral Polarimetric Glucose Detection Using a Single Pockels Cell," Optical Engineering 33(8):2746-53 (1994).
Kohl, M. et al., "Influence of Glucose Concentration on Light Scattering in Tissue-Simulating Phantoms," Optics Letters 19(24):2170-72 (1994).
Kohl, M. et al., "The Influence of Glucose Concentration Upon the Transport of Light in Tissue-Simulating Phantoms," Phys. Med. Biol. 40:1267-87(1995).
Kruse-Jarres, J.D., "Physicochemical Determinations of Glucose in Vivo," J. Clin. Chem. Clin. Biochem. 26(4):201-08 (1988).

(56) References Cited

OTHER PUBLICATIONS

Larin, K.V. et al., "Noninvasive Blood Glucose Monitoring With Optical CoherenceTomoqraphy," Diabetes Care 25(12):2263-67 (2002).

Larin, K.V. et al., "Phase-Sensitive Optical Low-Coherence Reflectometry for the Detection of Analyte Concentrations," Appl. Optics 43(17):3408-14 (2004).

Larin, K.V. et al., "Specificity of Noninvasive Blood Glucose Sensing Using Optical Coherence Tomography Technique: A Pilot Study," Physics in Med. & Biol. 48:1371-90 (2003).

Larin, K.V. et al., "Optoacoustic Signal Profiles for Monitoring Glucose Concentration in Turbid Media," SPIE Proc. 3726:576-83 (1988).

Lide, D.R., CRC Handbook of Chemistry and Physics, 79th ed. (CRC Press, Boca Raton, Florida, 1998).

Mackenzie, H.A. et al., "Advances in Photoacoustic Noninvasive Glucose Testing," Clin. Chem. 45(9):1587-95 (1999).

Maier, J.S. et al., "Possible Correlation Between Blood Glucose Concentration and the Reduced Scattering Coefficient of Tissues in the Near Infrared," Optics Lett. 19(24):2062-64 (1994).

March, W. et al., "Optical Monitor of Glucose," Trans. Am. Soc. Artif. Intern. Organs 25:28-31 (1979).

March, W.F. et al., "Noninvasive Glucose Monitoring of the Aqueous Humor of the Eye: Part II. Animal Studies and the Scleral Lens," Diabetes Care 5(3):259-65 (1982).

Mendelson, Y. et al., "Blood Glucose Measurement by Multiple Attenuated Total Reflection and Infrared Absorption Spectroscopy," IEEE Trans. Biomed. Eng. 37(5):458-65 (1990).

Moreno-Bondi, M,C. et al., "Oxygen Optrode for Use in a Fiber-Optic Glucose Biosensor," Anal. Chem. 62(21):2377-80 (1990).

Muller, A., "In Vivo Measurement of Glucose Concentration with Lasers," Harm. Metab. Res. Suppl. 8:33-35(1979).

Narayanaswamy, R., "Current Developments in Optical Biochemical Sensors," Biosens. Bioelectron. 6(6):467-75 (1991).

Pan, S. et al., "Near-Infrared Spectroscopic Measurement of Physiological Glucose Levels in Variable Matrices of Protein and Triglycerides," Anal, Chem. 68:1124-35 (1996).

Peterson, J.I. et al., "A Miniature Fiberoptic pH Sensor Potentially Suitable for Glucose Measurements," Diabetes Care 5(3):272-74 (1982).

Quan, K.M. et al., "Glucose Determination by a Pulsed Photoacoustic Technique—An Experimental Study Using a Gelatin-Based Tissue Phantom," Phys. Med. Biol. 38(12): 1911-22 (1993).

Rabinovitch, B. et al., "Noninvasive Glucose Monitoring of the Aqueous Humor of the Eye: Part I. Measurement of Very Small Optical Rotations," Diabetes Care 5(3):254-58 (1982).

Robinson, M.R. et al., "Noninvasive Glucose Monitoring in Diabetic Patients: A Preliminary Evaluation," Clin. Chem. 38(9):1618-22 (1992).

Robinson, R.J, et al., "Glucose-Sensitive Membrane and Infrared Absorption Spectroscopy for Potential Use as an Implantable Glucose Sensor," ASAIO J. 38(3):M458-62 (1992).

Rusch, T.L. et al., "Signal Processing Methods for Pulse Oximetry," Comput. Biol. Med. 26(2):143-59 (1996).

Ruth, Bernhard, et al. "Noncontact determination of skin blood flow using the laser speckle method: Application to patients with peripheral arterial occlusive disease (PAOD) and to type-1 diabetics." 1993. Wiley-Liss. Lasers in Surgery and Medicine. 13:179-188.

Schmitt, J.M. et al., "Measurement of Optical Properties of Biological Tissues By Low-Coherence Reflectometry," Appl. Optics 32(30):6032-42 (1993).

Schmitt, J.M. et al., "Speckle in Optical Coherence Tomography," J. Biomed. Optics 4(1):95-105 (1999).

Schmitt, J.M. et al., "Optical Coherence Tomography (OCT): A Review," IEEE J. Selected Topics in Quantum Electronics 5(4):1205-15 (1999).

Sevick, E.M. et al., "Near-Infrared Optical Imaging of Tissue Phantoms with Measurement in the Change of Optical Path Lengths," Adv. Exp. Med. Biol. 345:815-23 (1994).

Sodickson, L.A. et al., "Kromoscopic Analysis: A Possible Alternative to Spectroscopic Analysis for Noninvasive Measurement of Analytes in Vivo," Clin. Chem. 40(9):1838-44 (1994).

Star, W.M. et al., "Light Dosimetry: Status and Prospects," J. Photochem. Photobiol. 1(2):149-67 (1987).

Stoddart, S. et al., "Pulse Oximetry: What it is and Howto Use it," J. Neonatal Nursing 10:12-14 (1997).

Takai, N. et al., "Studies of the Development of Optical Fiber Sensors for Biochemical Analysis," Artif. Organs 15{2}:86-89 (1991).

Tunchin, V.V. et al., "Light Propagation in Tissues with Controlled Optical Properties," J. Biomed. Opt. 2(4):401-17 (1997).

Wang, L. et al., "Speckle Reduction in Laser Projection Systems by Diffractive Optical Elements," Appl. Optics 37(10):1770-75 (1998).

Weast, R.C., et al., CRC Handbook of Chemistry and Physics, $70^{th}$ ed., (CRC Cleveland, Ohio, 1989).

Welch, A.J. et al., Practical Models for Light Distribution in Laser-Irradiated Tissue, Lasers Surq. Med. 6(6):488-93 (1987).

Wicksted, J.P. et al., "Monitoring of Aqueous Humor Metabolites Using Raman Spectroscopy," SPIE Proc. 2135:264-74 (1994).

Zeller, H. et al., Blood Glucose Measurement by Infrared Spectroscopy,• J. Artif. Organs 12(2):129-35 (1989).

Zhao, Yonghua, et al. "Doppler standard deviation imaging for clinical monitoring of in vitro human skin blood flow." Optics Letters. Sep. 15, 2000. vol. 25, No. 18 pp. 1358-1360.

\* cited by examiner

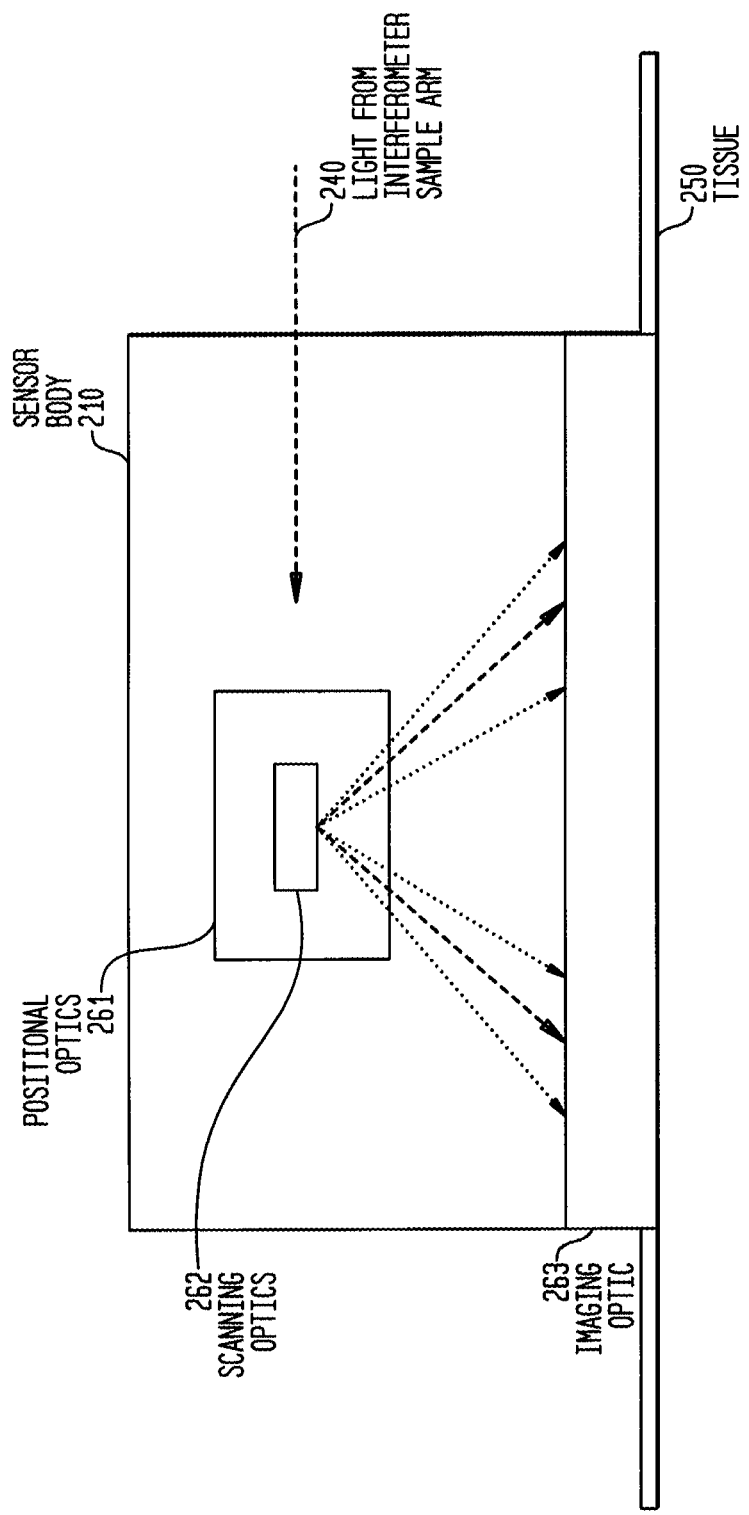

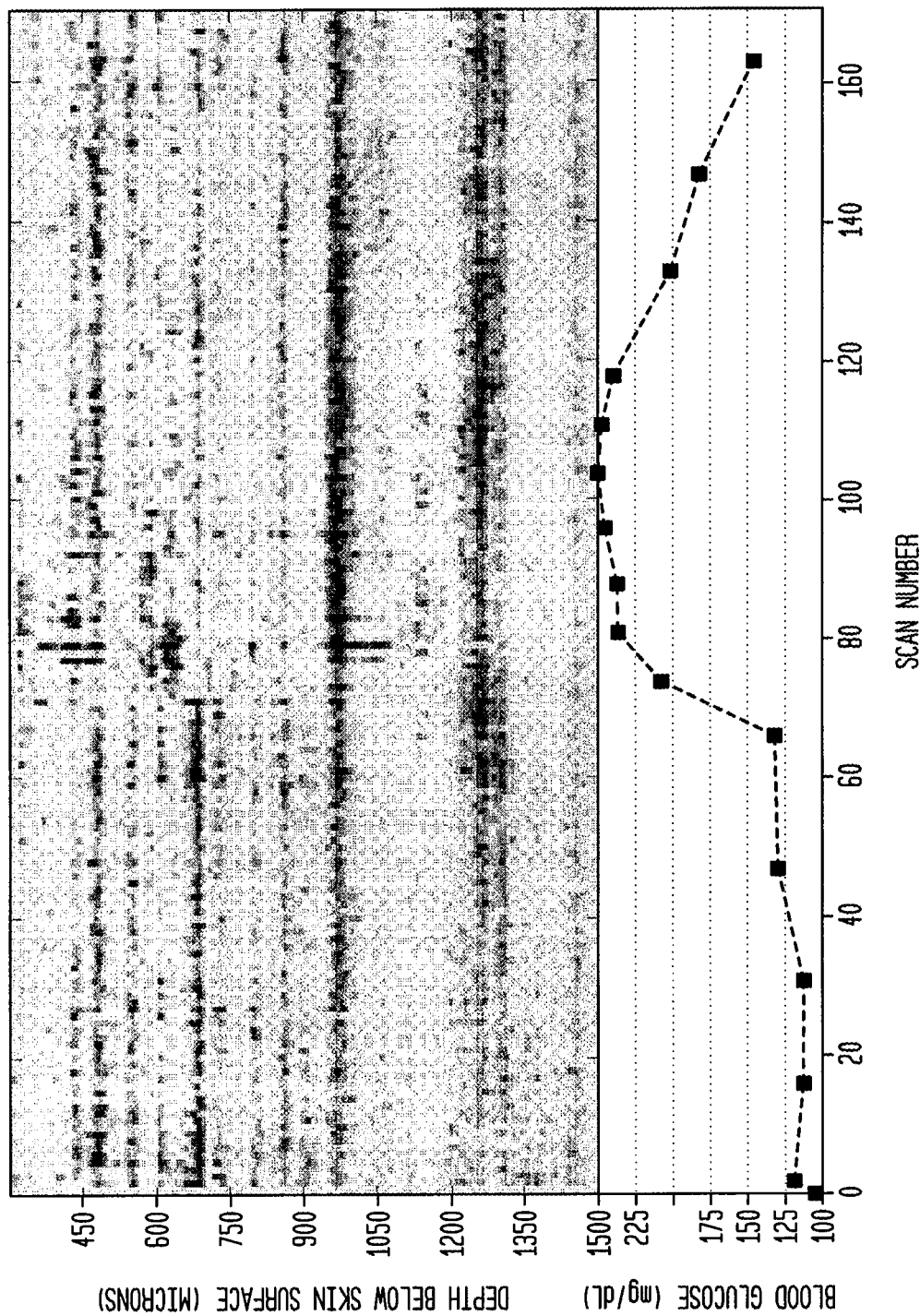

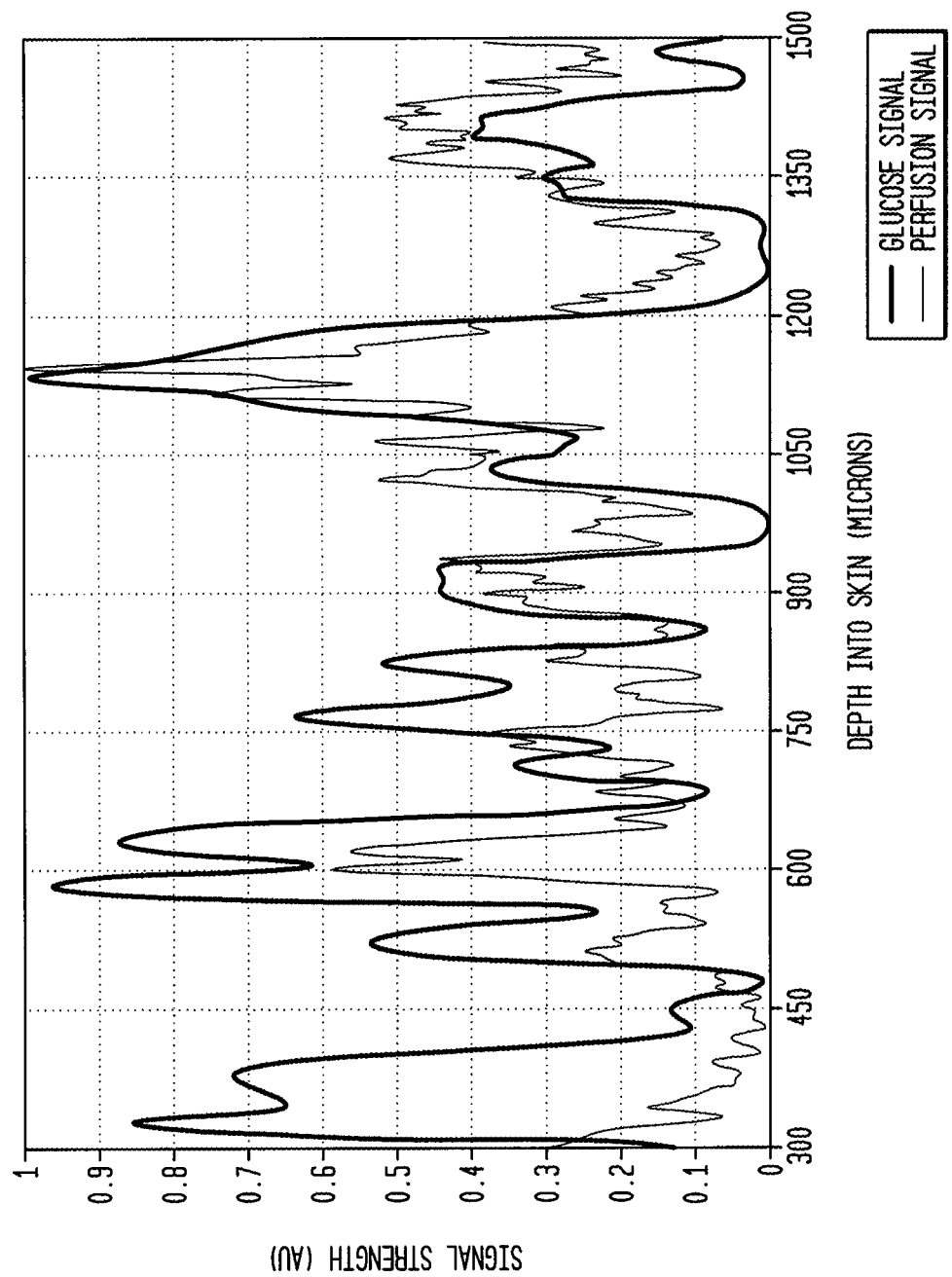

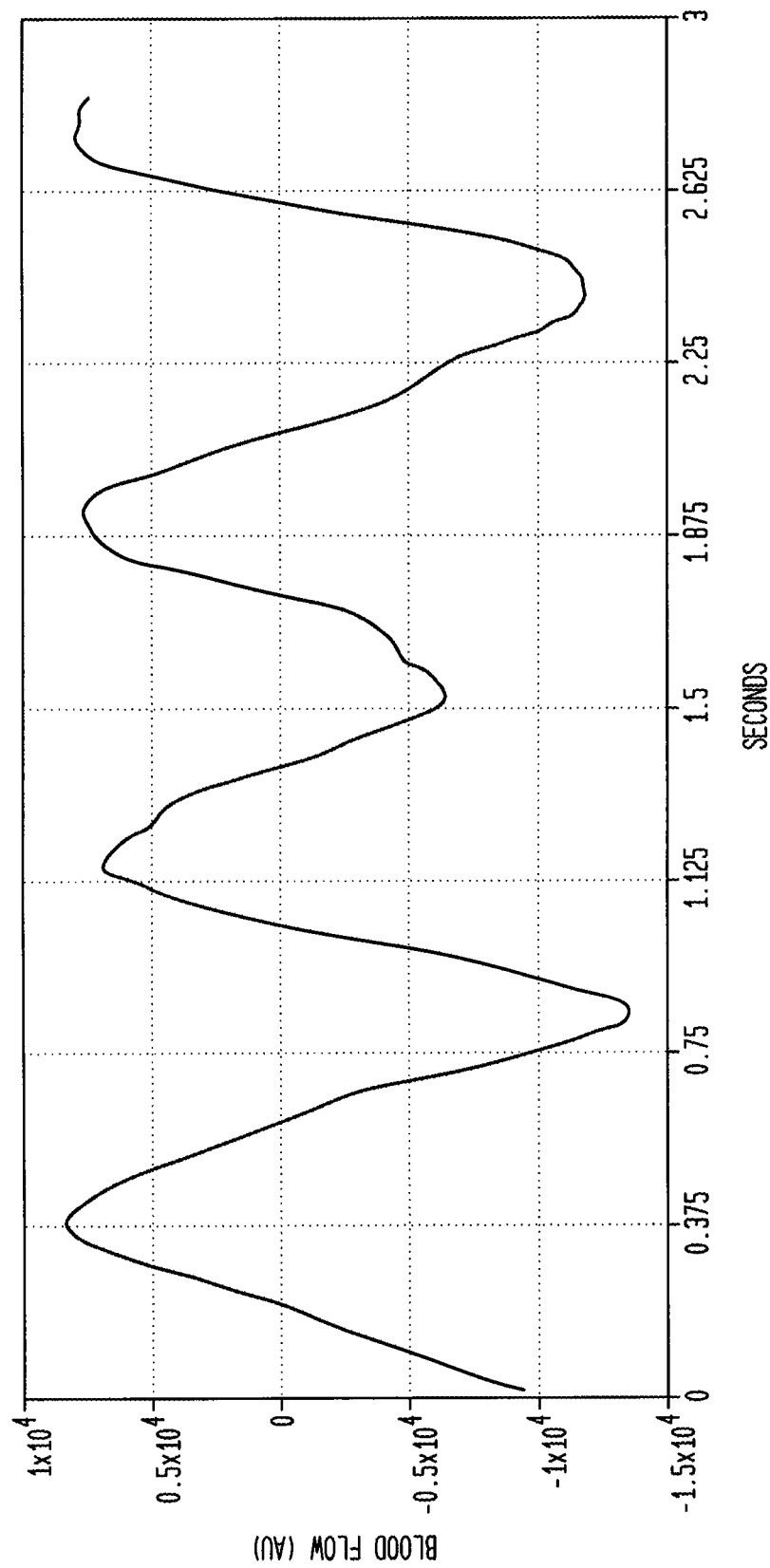

FLOWOMETRY IN OPTICAL COHERENCE TOMOGRAPHY FOR ANALYTE LEVEL ESTIMATION

CROSS-REFERENCE TO RELATED APPLICATIONS

The present application is a continuation of U.S. patent application Ser. No. 14/711,610, filed May 13, 2015, titled "Flowometry in Optical Coherence Tomography for Analyte Level Estimation," which is a continuation of U.S. patent application Ser. No. 14/063,977, filed Oct. 25, 2013, titled "Flowometry in Optical Coherence Tomography for Analyte Level Estimation," which is a continuation of U.S. patent application Ser. No. 12/397,593, filed Mar. 4, 2009, titled "Flowometry in Optical Coherence Tomography for Analyte Level Estimation," which claims the benefit of U.S. Provisional Application No. 61/068,058, filed Mar. 4, 2008, titled "Flowometry in Optical Coherence Tomography for Analyte Level Estimation," and U.S. Provisional Application No. 61/033,584, filed Mar. 4, 2008, titled "Multispot Monitoring for Use in Optical Coherence Tomography." The present application is also related to U.S. patent application Ser. No. 12/397,577, filed Mar. 4, 2009, titled "Multispot Monitoring for Use in Optical Coherence Tomography." The entirety of each of the above-mentioned applications is hereby incorporated by reference herein for all purposes.

BACKGROUND

The present application relates to methods and devices for performing measurements with optical coherence tomographic techniques, and in some instances particularly for detecting analytes using optical coherence tomography.

Optical coherence tomography (herein "OCT") is an optical imaging technique that has shown great promise for use in many applications such as glucose monitoring. In this sensor modality, the high depth resolution of this technique is able to measure, with a high degree of accuracy, the scattering properties of a subject's tissue (e.g., the skin). These scattering properties can be sensitive to the changes in analyte levels in a subject's tissue. e.g., blood glucose levels in a subject. Thus, changes in the OCT signal can be correlated with changes in the analyte levels and thus serve as a prospective predictor of changes in that subject's analyte levels.

While OCT-based devices and techniques have shown promise in detecting analytes such as glucose, improvements are still needed. For instance, improvements in the speed and ease with which such techniques can be applied could help commercial acceptability of such devices. Accordingly, a need persists to provide improved OCT devices and techniques, which can provide accelerated estimates of analyte levels in a subject's tissue in an easy to use and reliable manner.

SUMMARY

Optical coherence tomography (herein "OCT") based analyte monitoring systems are disclosed. In one aspect, techniques are disclosed that can identify fluid flow in vivo (e.g., blood flow), which can act as a metric for gauging the extent of blood perfusion in tissue. For instance, if OCT is to be used to estimate the level of an analyte (e.g., glucose) in tissue, a measure of the extent of blood flow can potentially indicate the presence of an analyte correlating region, which would be suitable for analyte level estimation with OCT. Another aspect is related to systems and methods for scanning multiple regions. An optical beam is moved across the surface of the tissue in two distinct manners. The first can be a coarse scan, moving the beam to provide distinct scanning positions on the skin. The second can be a fine scan where the beam is applied for more detailed analysis.

Some aspects of the present invention are directed to techniques which can detect fluid flow in vivo (e.g., blood flow) using optical coherence tomography (herein "OCT"). Such techniques can utilize the speckle from an OCT scan and/or the fringe-frequency modulation to identify flow. Detection of flow by OCT can be used in a variety of applications such as heart monitoring or imaging of fluid flow in a non-invasive manner. In some embodiments, OCT is applied to detect blood flow, which can act as a metric for gauging the extent of blood perfusion in tissue. For instance, if OCT is to be used to estimate the level of an analyte (e.g., glucose) in tissue, a measure of the extent of blood flow can potentially indicate the presence of an analyte correlating region (herein "ACR") which would be suitable for analyte level estimation with OCT. While not necessarily being bound by any particular theory, if a particular analyte is typically associated with blood (e.g., related to the presence of arterioles and venules), the identification of blood perfused tissue can act as a marker of where detailed OCT measurements and/or analysis of measurements should be performed to obtain estimates of analyte levels. Accordingly, some embodiments are directed to methods and device for analyte level estimation using OCT, where OCT scanning can identify tissue regions having blood flow that are suitable for analyte estimation.

For example, exemplary embodiments are drawn toward systems and methods of determining blood analyte levels in a tissue sample using optical coherence tomography (OCT). In an exemplary method, a plurality of regions in the tissue sample are scanned using OCT to provide corresponding intensity data measurements. Each tissue region can be raster scanned to provide the intensity data. The tissue regions can optionally be scanned over multiple depths. The intensity measurements can include signals from backscattered light and/or can exhibit speckle. The intensity data measurements, and/or speckle, can be analyzed to determine whether blood flow is present in the corresponding region. Blood analyte levels can be obtained from one or more of the regions having blood flow present as analyzed from the OCT measurements.

Scanning of a tissue sample can be performed in a variety of manners. In some instances, multiple regions are scanned over multiple moments in time to provide the intensity measurements. Comparison of intensity data, which can exhibit speckle, taken over the multiple time moments can be used to determine whether blood flow is present. In some instances, intensity data measurements are compared over multiple tissue regions to determine whether blood flow is present.

Other aspects of the invention are directed to systems for determining at least one blood characteristic in a tissue sample. The system can comprise an OCT apparatus configured to obtain intensity data measurements from a plurality of regions in the tissue sample. Such systems can be consistent with any of the OCT systems disclosed in the present application and/or those within the knowledge of one skilled in the art. The system can further comprise a processor configured to analyze the intensity data measurements from the OCT apparatus to determine whether blood blow is present in at least one region. In some instances, the system can be configured to provide different intensity data measurements over a plurality of regions and a plurality of depths. The system can also be configured to provide raster scans of a plurality of regions. Systems that provide scanning over different regions can utilize a beam scanner, which can be appropriately configured to achieve the desired scanning modality. In some embodiments, the OCT apparatus can be configured to provide different intensity data measurements over a plurality of moments in time.

In related embodiments, the processor can be configured to convert the intensity data measurements into analyte levels (e.g., blood glucose levels). The processor can be configured to analyze speckle in the intensity data measurements and optionally compare those measurements to determine whether blood flow is present. In other embodiments, the processor can analyze fringe-modulated data, such as high frequency components and/or amplitude modulation. The processor can also comprise a signal filter for converting at least a portion of the intensity data measurement into a reduced intensity signal, which can indicate the presence of blood flow through the correlation with fringe frequency modulation. The signal filter can comprise a narrow and/or wide band filter to convert at least a portion of the intensity data measurements into an attenuated output, with the processor optionally configured to compare the reduced intensity signal and the attenuated output to determine the presence of blood flow.

In some exemplary embodiments, a method is utilized to determine the presence of fluid flow in tissue using OCT. These embodiments can optionally be combined with other steps to determine blood analyte levels, as described herein. A tissue sample can be scanned over each of one or more tissue regions, for example at various depths, to obtain corresponding fringe-modulated data, which can be analyzed to determine the presence of blood flow. The fringe-modulated data to be analyzed can include determining a peak fringe frequency shift, or analyzing the amplitude modulation in the data, to determine whether blood flow is present. In the latter case, selected high frequency components of the intensity data, which can be related to speckle, can be analyzed to determine whether blood flow is present. In some instances, the intensity data measurements having fringe-modulated data can be passed through a filter, wherein the filter is configured to produce a filtered signal indicating fringe frequency modulation indicative of blood flow's presence. For example, the intensity data measurements can be passed through a narrow band filter, which can be configured to produce a reduced intensity signal output from an intensity data measurement exhibiting blood flow. Optionally, the intensity data measurements can also be passed through a wide band filter, which can be configured to produce an attenuated output exhibiting at least one fringe-modulated feature from an intensity data measurement exhibiting blood flow. Subsequently, the reduced intensity output and the attenuated output can be compared to determine whether blood flow is present. Digital signal processing, analog signal processing, or a combination of the two techniques can be utilized to analyze the intensity data measurements in any fashion.

Other aspects of the present invention are directed to methods, devices, and/or systems that can scan multiple tissue sites. Tissue sites can each be scanned using an optical coupler, which can be attached to a single location on a subject's skin; each tissue site can also, or alternatively, be associated with a separate potential analyte correlating region (herein "ACR") or be separated by a distance at least as large as some distance associated with an ACR. An assessment of the quality of each tissue site to provide acceptable analyte levels (i.e., that the site is a ACR) can be made, followed by analyzing OCT data at one or more of the identified ACRs to provide an estimate of an analyte level in the scanned tissue. Other aspects of devices and methods that embody some or all of these features are included in the present application.

For instance, some embodiments are drawn toward OCT-based analyte monitoring systems in which the optical interrogation beam is moved across the surface of the tissue in two distinct ways. The first is a coarse tune of the beam position, moving the beam over a large distance in order to provide positions on the skin that are spatially distinct from each other. The second is a fine scan where the beam is applied over one or more smaller areas that are selected by a controller for more detailed analysis.

Coarse position tuning over a large area of tissue can be useful when the tissue is inhomogeneous so that regions of little or no analytic value can be ignored or discounted, and/or regions of high analytic content can be identified for future analysis. For example, hairs with their associated structures (i.e., sebaceous glands, erector muscles, etc.) can be avoided. These structures are large and, due to the depth at which their blood vessels lie, have little to no associated perfusion in the dermis. Thus, coarse scanning over a large spatial area allows the sensor to avoid such structures. Another example is an arteriole and/or venule plexus, a highly perfused region of tissue, and a desirable scanning location for the sensor. These structures are more sparsely distributed and thus coarse scanning over a large area is desirable to ensure that such a plexus can be located. In both cases, the location of these structures cannot easily be discerned by the naked eye and thus the sensor can also accommodate for sub-optimal sensor placement by the user.

The fine or raster portion of the scan can provide a smaller region of tissue from which data is obtained to correlate to glucose changes. The fine scan takes advantage of the high spatial resolution of the system and allows regions of the tissue with a high density of analyte correlating regions (ACRs) to be monitored, improving the system response to glucose.

Some exemplary embodiments are drawn toward optical coherence tomography (OCT) systems for determining an analyte level in tissue. The systems, which can optionally be a non-imaging system unlike many other OCT systems, can include a light source for generating skin-penetrating radiation suitable for OCT measurements and a detector for receiving reflected light from the skin-penetrating radiation. An interferometer can be coupled to the system to form a combined signal from the reflected light from the skin and a reference beam, the combined signal being received by the detector. A phase shifter can be included and configured to shift the phase of the reference beam, which can provide tissue depth scanning.

A beam scanner can be included for directing a beam of radiation from the source to a plurality of sites to provide a measure of analyte levels (e.g., glucose levels) in the tissue at one or more of the sites. Each site can be associated with a different analyte correlating region. For instance, each site can include a non-overlapping area (e.g., each site being a unique spatial area) relative to all other sites. The sites can form a selected pattern and/or substantially cover a designated larger tissue area. The beam scanner can scan within a tissue site in a variety of manners. For example, the scanner can scan the entire area of at least one of the plurality of sites and/or scan in a manner to provide an aggregated OCT measurement that has reduced speckle content. Scanning within a tissue area can be conducted to provide OCT data sufficient to provide an analyte level estimation and/or sufficient to provide a measure of validity of a tissue site as an ACR.

In some embodiments, a beam scanner, which can be part of an OCT apparatus for detecting analyte levels in scanned tissue, can be configured to adjust movement of a beam on at least two-different length scales. One of the length scales can be a site-scale where the beam moves over a distance large enough such that the beam scanner probes a plurality of tissue sites. Another length scale can be a measurement-scale wherein the beam moves over a distance smaller than the site-scale. OCT measurements can be taken over the measurement-scale such that the data obtained can provide analyte measurement correlation.

Beam scanners can include one or more optical elements (e.g., mirror or rotatable prism) configured to move a beam of radiation. For instance a rotatable prism can be used to move the beam to a variety of tissue sites, while a movable mirror can provide scanning within a tissue site. Other types of devices, such as a flexure, can also be used to control optical element movement.

Also, a controller can be included for selecting sites from the plurality of sites for monitoring. The controller can be integrated into a single unit with a beam scanner, or be a separate device coupled to the beam scanner. The controller can be configured to associate OCT measurements with each of the plurality of sites, and can subsequently provide an aggregated measure of the analyte level using OCT measurements from a plurality of sites. OCT measurements can correspond with a measure of an analyte level in the scanned tissue. In some instances, the controller can be configured to select one or more sites based on whether a site is validated for analyte level measurement (e.g., whether the site is validated based upon a tissue hydration level). OCT measurements from one or more validated site scan be used to calibrate an OCT system.

Some embodiments are directed toward a structure for providing a coupling between an optic and a subject during OCT measurements. One or more optical elements can be optically couplable to an OCT system to guide reflected light. A patch for aligning the optical element with skin of the subject can be included. The patch can include a rigid body coupled to the optical element. The rigid body can be configured to stabilize optical path lengths between the optical element and the skin. A plurality of pliable extensions can be coupled to the rigid body. Each pliable extension can extend away from the rigid body, and can be configured to hinder movement of the rigid body relative to the skin. In some instances, a patch for providing a coupling between an optic and a subject during OCT measurements can have an optical element and a moisture-removing structure configured to contact skin of the subject. The moisture-removing structure can be configured to transport moisture away from the skin of the subject to hinder moisture build up at an interface between the optical element and the skin. Moisture removing structures can include a moisture-absorbent material, and/or a perforated hydrophilic material.

Other embodiments are directed to methods for performing OCT measurements to determine an analyte level in tissue, such as a blood glucose level. Such methods can be implemented without the need to form and/or process an image. An OCT system can be aligned to a subject through an optical coupler. Then a beam can be scanned over a first tissue site using the attached optical coupler to collect a first set of OCT measurements. Such scanning can combine light reflected from scanning a designated tissue site with a reference beam to produce an interference signal, which can be processed to aid determination of the analyte level in the tissue. The beam can then be scanned over one or more other sites to provide corresponding OCT measurements. Each tissue site can be spatially distinct from the one or more of the other tissue sites. The tissue sites can also form a selected pattern. Scanning within a tissue site can include scanning the beam over the entire spatial area of the tissue site and/or scanning to provide data to obtain an analyte level which can reduce the effect of speckle. A plurality of depths can also be scanned.

Specific sites can be selected from the scanned sites for monitoring analyte levels, with the corresponding OCT measurements being processed to measure the analyte level in the tissue. The selection of sites can include designating whether one or more sites is associated with a validated site. This can be determine, for example, by determining whether corresponding OCT measurements indicate a selected level of tissue hydration. If a two or more sites are validated and corresponded with a measure of an analyte level, the plurality of levels can be aggregated into an aggregated measure of analyte levels in the tissue, which can be used to calibrate an OCT system. Alternatively, data from validated sites can be used to calibrate an OCT system without aggregating the data.

BRIEF DESCRIPTION OF THE DRAWINGS

The present application will be more fully understood from the following detailed description taken in conjunction with the accompanying drawings (not necessarily drawn to scale), in which:

FIG. 2 is a schematic diagram of a beam scanner implemented to scan tissue, according to one embodiment of the present invention;

FIG. 13 provides graphs of a difference signal from OCT scanning at varying tissue depths as a function of time, and a corresponding graph of measurements of blood glucose values as a function of time, according to some embodiments of the present invention;

FIG. 14 provides a graphs showing overlapping traces of a perfusion signal and a glucose signal derived from the data shown in FIG. 13; and FIG. 15 provides a graph of pulsatile blood flow from OCT blood flow measurements, according to an embodiment of the present invention.

DETAILED DESCRIPTION

Figure 1:
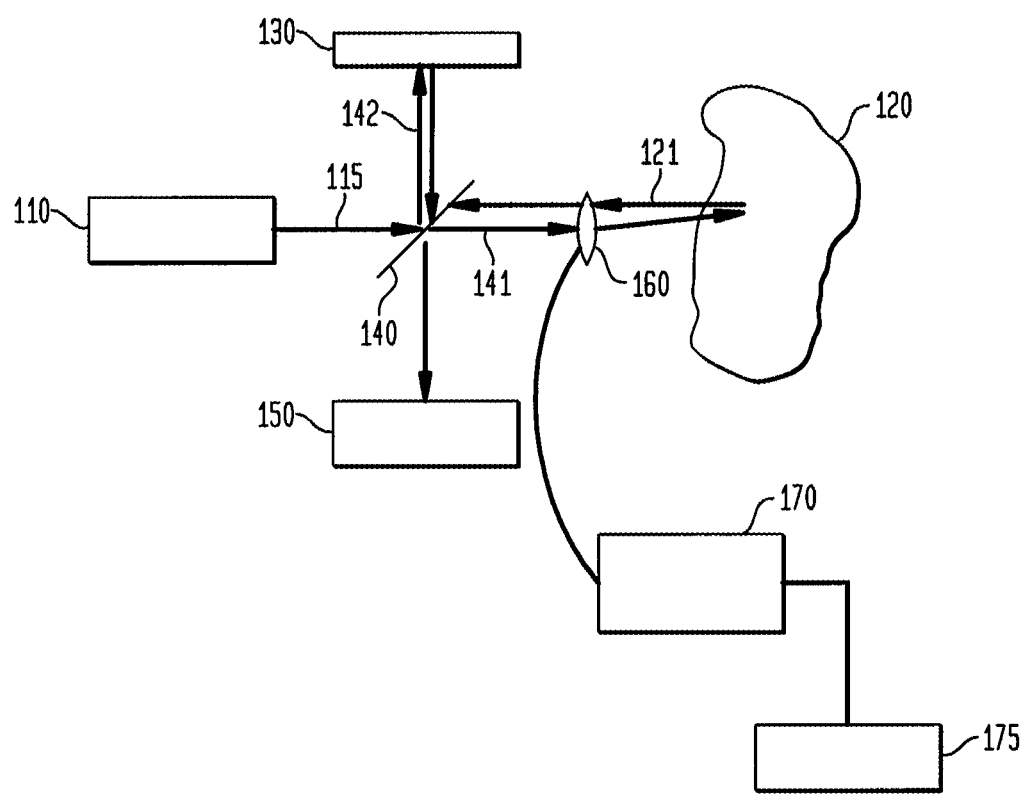
FIG. 1 is a schematic diagram of an OCT system, consistent with an embodiment of the present invention.

Aspects of the present application that are consistent with some embodiments described herein can improve the use of OCT to determine analyte levels. The type of analytes that can be identified can include any analyte capable of being detected with OCT. In many instances, these analytes are water-based analytes and/or analytes that are present in blood perfused tissue. Examples include oxygen, hemoglobin, glucose, water, components of blood, and other analytes present in tissues or other samples. In many embodiments herein, glucose is an analyte of interest. An analyte correlating region (ACR) is a region of a subject's tissue in which OCT can be applied to provide an accurate estimate of an analyte's level in the tissue. Accordingly, using OCT to provide measurements substantially within a ACR can yield data allowing an accurate estimate of the analyte level.

For a selected analyte, regions of the tissue in which an OCT signal is sensitive to changes in the analyte level are not typically uniformly distributed, either as a function of depth or laterally across the tissue. For example, analytes that are present in blood perfused tissue (e.g., glucose) can be non-uniformly distributed due to the non-uniform distribution of blood vessels in the tissue. In particular, the potentially high resolution of OCT, both depth and lateral, enables the location of ACRs, for example glucose correlating regions (herein "GCRs"), to be identified. However, since the resolution of an individual OCT measurement is typically much higher than the scale of many ACRs, it can be difficult to insure that these regions will exist at a given tissue location which is scanned using conventional techniques. Thus, for example, an OCT glucose monitor's performance in the past has been highly dependent on the location of the skin upon which the sensor is placed.

Though OCT can be applied using a brute force technique, analyzing a large tissue region in depth and extent followed by extensive data analysis to isolate portions of the data that do correspond with good ACRs, such a methodology is costly in terms of time and effort expended to produce accurate analyte level readings. As well, the equipment and data processing commensurate with such effort can be a financial burden. Accordingly, if one can utilize an OCT technique to quickly identify tissue regions with substantial blood flow, more extensive OCT measurements can potentially be performed, and data analyzed, therewith to yield faster and more accurate results. In addition, the identification of ACRs can be beneficial by reducing the effort needed to utilize OCT to accurately identify an analyte level. Furthermore, if ACRs can be identified more readily, OCT measurements can be less dependent upon the placement of the sensor vis-à-vis the patient's skin location. Some embodiments of the present invention can potentially address some of these problems. By utilizing embodiments disclosed herein, such as techniques that provide multiple tissue site OCT sensing and/or assessing whether the spots are ACRs, (e.g., by blood flow detection) an OCT technique can focus data gathering or analysis on the ACR regions to collect an analyte level without performing unneeded data collection and/or analysis on regions which do not correlate analyte levels acceptably.

Other potential advantages can also be accrued. For instance, sensor placement by the user can be less critical. Since the ACRs within the tissue are not visible to the unaided eye, it is not possible for the user to place the sensor on a region of tissue that has these structures. Further, there are structures within tissue that do not correlate with analyte changes, such as sebaceous glands associated with hairs in skin when attempting to sense glucose. In this case again, sebaceous glands are not visible to the user, thus a sensor with the ability to monitor multiple tissue sites over a wide spatial extent provides less sensitivity to sensor placement.

In another instance, monitoring multiple tissue sites potentially provides multiple signals that can be used to improve the sensitivity, stability, and signal-to-noise levels of an OCT system relative to the analyte changes in the subject.

Also, diversity of tissue sites can provide stability to the OCT system's analyte correlation by minimizing the effects of physiologic variances in a subject during monitoring. An example of this would be changes in microcirculation on the subject from pharmacologically or temperature induced changes. In this case, tissue sites where the blood perfusion changes dramatically (up or down) can identified and weighted by the sites where the perfusion remained more constant generating a more stable output of the sensor.

Systems and Devices for OCT Scanning

Some embodiments are directed to systems for performing OCT to determine the presence of blood flow in a scanned tissue region. Some additional embodiments are directed to systems for performing OCT to determine an analyte level in tissue. Other embodiments combine such detection with other features to perform analyte level estimation with an OCT system. Such embodiments can utilize an OCT system to provide data intensity measurements that are analyzed by a processor. Exemplary OCT systems can include a number of components such as a light source for generating skin-penetrating radiation suitable for OCT measurements, interferometers, and/or a detector for receiving reflecting light from the skin-penetrating radiation. The system can also include a beam scanner, which can be used to direct a beam of radiation from the source to one or more tissue sites. Beam scanners can include devices that operate in accord with the disclosure of the present application and/or operate in a conventional manner. Data collected from one or more of the sites can be processed by a processor to provide a measure of the presence of blood flow or the measure of analyte levels at the respective sites using any combination of the methodologies disclosed herein and/or known to those skilled in the art. The term "processor" is used generally to include any actual number of devices configured to perform the designated processes. Accordingly, a processor can be embodied as any combination of a programmable unit, a microprocessor, an embedded preprogrammed processor, a stand-alone computing unit, or other devices and configurations as understood by those skilled in the art. The system can also include a controller, which can be used to designate a tissue site associated with blood flow or can be used to select one or more of the multiple sites for further processing (e.g., extracting analyte data therefrom).

As utilized herein, a tissue site can be a selected tissue region (e.g., an area or volume of the tissue) which can be probed using OCT. In many instances, a tissue site has a geometrical size larger than the resolution of the OCT system. Accordingly, in some instances, the tissue site is at least large enough to allow an OCT system to perform scanning within the site, which can potentially lead to data of an analyte level within the site.

Some exemplary embodiments of OCT systems can be described with reference to the schematic diagram of an OCT system shown in FIG. 1. A light source 110 is used to generate skin-penetrating radiation 115 suitable for OCT measurements. A interferometer is employed to perform the measurement. For example, the interferometer can include a beam splitter 140 which can direct a measurement light beam 141 to an optical element 160 and a reference light beam 142 to a phase shifter 130 (e.g., a mirror). The sample beam 141 is directed by the optical element 160 to a tissue sample 120 (e.g., a skin portion of a subject). Light 121 is reflected from the tissue 120 and directed to the interferometer. The reference beam 142 is reflected by the phase shifter 130 back to the interferometer, where the phase shifter can be positioned to change the phase of the reflected light. The interferometer can combine the light from the phase shifter and tissue sample, and direct the light to a detector 150. The constructively interfered light will provide a signal to the detector 150. Such constructively interfered light thus interrogates a depth of the tissue 120 selected by the distance traveled by the sample beam 142 to the phase shifter 130. As used herein, tissue depth is typically the shortest distance from a location in the tissue to a tangent plane on the tissue surface.

In some embodiments where fringe frequency modulation is utilized, the phase shifter 130 is moved at a constant velocity V, which results in a fringe frequency proportional to the ratio of V to the wavelength of the radiation. When the sample beam strikes a moving target, this fringe frequency is modulated. Accordingly, some embodiments herein utilize the modulation of the fringe frequency to detect blood flow.

The general use of OCT systems to provide estimates of analyte levels in tissues is described in a number of references. For example, U.S. Pat. No. 7,254,429 provides descriptions of methods, devices, and systems which can be used to perform OCT measurements in tissue; U.S. Patent Application Publication No. U.S. 2006/0264719 A1 provides techniques for calibrating an OCT system for performing analyte measurements; and U.S. Patent Application No. U.S. 2006/0276696 A1 provides techniques for performing analyte measurements and calibration that include the use of multiple wavelengths of radiation. The teachings of each of these references is included herein in their entirety. Accordingly, OCT systems consistent with embodiments herein can utilize any one or combination of features of OCT systems described in the references herein. For example, in some embodiments, the light source is a low coherence source, and/or the system can be specifically configured for detecting glucose (e.g., blood glucose). OCT systems can be configured as non-imaging systems, which can optionally allow scanning of a tissue site such as to reduce the effect of speckle. In another example, the light source of an OCT system can utilize one or more wavelengths to enable glucose reading detection. Other aspects of OCT systems that can be utilized with embodiments herein can include features understood by those skilled in the art.

Beam Scanners and Controllers

Some embodiments herein include a beam scanner which can be configured to direct beams of radiation to one or more tissue sites for an OCT system. Such beam directing can be achieved in a variety of manners. For instance, as shown in FIG. 1, a beam scanner 170 can be coupled to one or more optical elements 160 to direct the beam to a particular site. A beam scanner, however, can also be coupled to any combination of optics and/or other light directing devices to provide the scanning. For example, the beam splitter, optionally in conjunction with one or more other optical elements, can also be coupled to the beam scanner such that the scanner can direct scanning of light impinging on a sample region. A controller 175 can also be included. The controller, which can be coupled to the beam scanner, can be used to facilitate operation of the beam scanner in a variety of manners (e.g., identify and/or direct which tissue sites should be utilized to provide an analyte measurement). A controller can be an integral portion of a beam scanner (e.g., within the inner workings of a single device) or can be embodied separately (e.g., as a processor of a microcomputer which is in electrical communication with a beam scanner). It should be understood that a beam scanner coupled with a controller can be part of an OCT system, or alternatively constitute an embodiment by itself.

The imaging optics of a beam scanner can be configured to have a variety of characteristics. First the optics can be configured to reduce variations in focal depth during the scanning at widely differing spatial positions. Also, the optical train of a beam scanner can be configured to limit unwanted spurious reflections that can corrupt the interferometer signal such as from optical surfaces at critical positions in the optical path. The numerical aperture of the optics can be selected to reduce the returned scattering signal while minimizing the confocal effect through the depth of interest in the skin. Aberrations due to far off axis scanning through the optic can also be desirably reduced.

Beam scanners can be configured to scan one or more tissue sites where the distinction between sites and the spatial extent of a particular tissue site can also be varied. For instance, each site can be chosen to have a unique region relative to every other site (i.e., none of the sites overlap). The sites can substantially cover a tissue section to be investigated, or can be distributed within a tissue section with space therebetween. The sites can form a selected pattern or can be randomly distributed therein. In some embodiments, the sites can be spaced farther apart than some characteristic length scale of an ACR. Such embodiments can allow an OCT system to quickly assess a tissue sample to locate ACRs where further measurements can be taken and/or analysis of particular measurements is to be performed to reduce the effort of data gathering and analysis. The characteristic length scale of an ACR can depend upon the analyte to be estimated and/or the type of tissue to be scanned. For example, with glucose correlating regions (GCRs), the characteristic length scale can be on a length associated with the distribution of blood vessels in a dermal region.

The spatial extent of a tissue site can also selected in a variety of geometries. For instance, different tissue sites can be distributed over a certain area with all the sites being substantially at the same depth. In other situations, the tissue sites can span a variety of depths and/or spatial extents, encompassing various volumes.

With regard to the size of a tissue site, as mentioned earlier, each tissue site can be a tissue region large enough that an OCT system can probe a variety of locations in the tissue site to determine an analyte level in the region (e.g., the region can be large enough so that analyte correlation in the region is possible). As well, the tissue site can be a region large enough to encompass an ACR, or to perform some other functionality associated with analyte detection (e.g., large enough to allow scanning therein to reduce speckle in an OCT system in which an analyte level is being estimated as described in U.S. Pat. No. 7,254,429). The tissue site can also be limited in size such that scanning in the site can be relatively rapid vis-à-vis scanning the entire area covered by a plurality of sites. The tissue size can also be limited such that such that the effects of structures that do not change with an analyte (such as a hair on glucose sensing) on one tissue site does not influence the signal received in another tissue site. The relative sizes each of the tissue sites can also vary, or be substantially uniform.

As well, the beam scanning can be performed using various data acquisition techniques to provide OCT data that can be used for a variety of purposes. For example, the scanning within a tissue sample can be sufficient to provide data allowing an analyte level measurement within the tissue sample. In another example, the scanning can provide data that allow validation of a site, as described herein, to determine whether a tissue site is an ACR which can provide good analyte level estimation. For instance, validation of a site can depend upon detecting the presence of blood flow. The latter example, can potentially lead to a more rapid data collection methodology where sites can initially be scanned for validation—and the validated sites are rescanned to provide more detailed OCT data for analyte level measurements within each validated site. Other varieties of scanning within a tissue site are also contemplated.

In some embodiments, beam scanners for use with OCT systems can adjust movement of a beam over multiple length scales, e.g., at least two different length scales. For instance, the beam scanner can move a beam over a site-scale, where the beam is moved over a distance large enough that the beam scanner probes a plurality of tissue sites within the distance of a coarse scale (e.g., site scale). Accordingly, the beam can interrogate a multiplicity of tissue sites (e.g., non-overlapping sites, and/or sites separated by a distance larger than a characteristic length of an ACR). The beam scanner can also be configured to move the beam over a measurement scale. Typically, the measurement scale is smaller than the coarse scale. OCT measurements can be taken within the measurement scale to provide an analyte level estimate in the tissue (e.g., the measurement scale has a size sufficient to allow analyte measurement correlation). It is understood that scanning over a coarse scale can incorporate any of the features regarding different tissue sites (e.g., the site-scale scans over tissue sites that do overlap one another), while scanning over the measurement scale can incorporate any of the features described herein regarding scanning within a tissue site (e.g., scanning in a tissue site to reduce speckle from a composite signal). It is understood that scanning can also be performed over additional length scales as well.

Some illustrations of features previously described with respect to beam scanners are described with reference to FIGS. 2 and 3A-3C. FIG. 2 provides an illustration of some features of particular embodiments of the present invention which utilize a beam scanner. The scanner 210 can comprise a body of a device with one or more optics 261, 262. The optics 261, 262 can be configured to direct light from an interferometer 240 to an imaging optic 263, which further directs the light to tissue 250. By configuring the optics 261, 262 appropriately, a beam that impinges upon tissue can be manipulated to provide multispot scanning. For example, one optic 261 can position the beam over multiple tissue sites, while another optic 262 can provide scanning within a tissue site, which can provide data for analyte measurements. Alternatively, a single optic can provide both the coarse and fine scanning functions (e.g., a galvanic reflecting mirror driven for large scale beam displacements in the coarse tuning mode and fine dithering in the analytic mode).

Figure 3A:
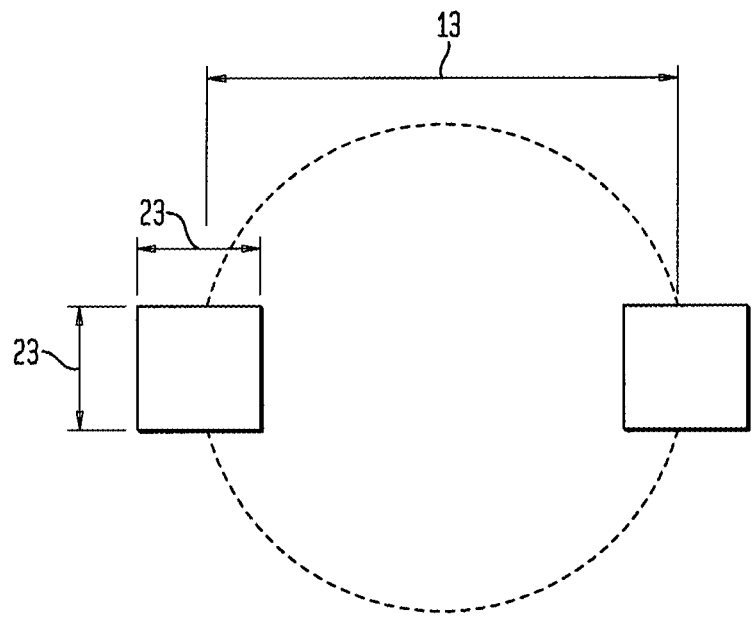
FIG. 3A is a schematic diagram of a number of tissue sites to be scanned oriented around a circular path, according to one embodiment of the present invention.
Figure 3B:
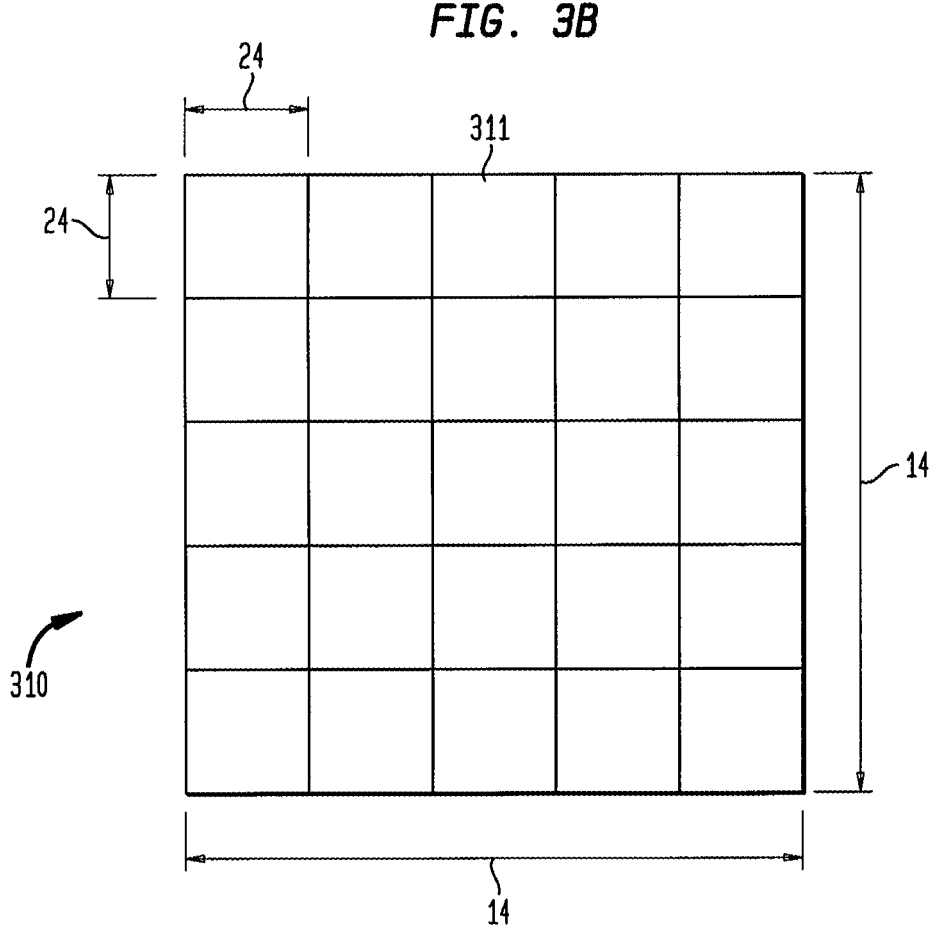
FIG. 3B is a schematic diagram of a number of tissue sites to be scanned oriented in a gridded pattern to substantially cover a tissue area, according to another embodiment of the present invention.
Figure 3C:
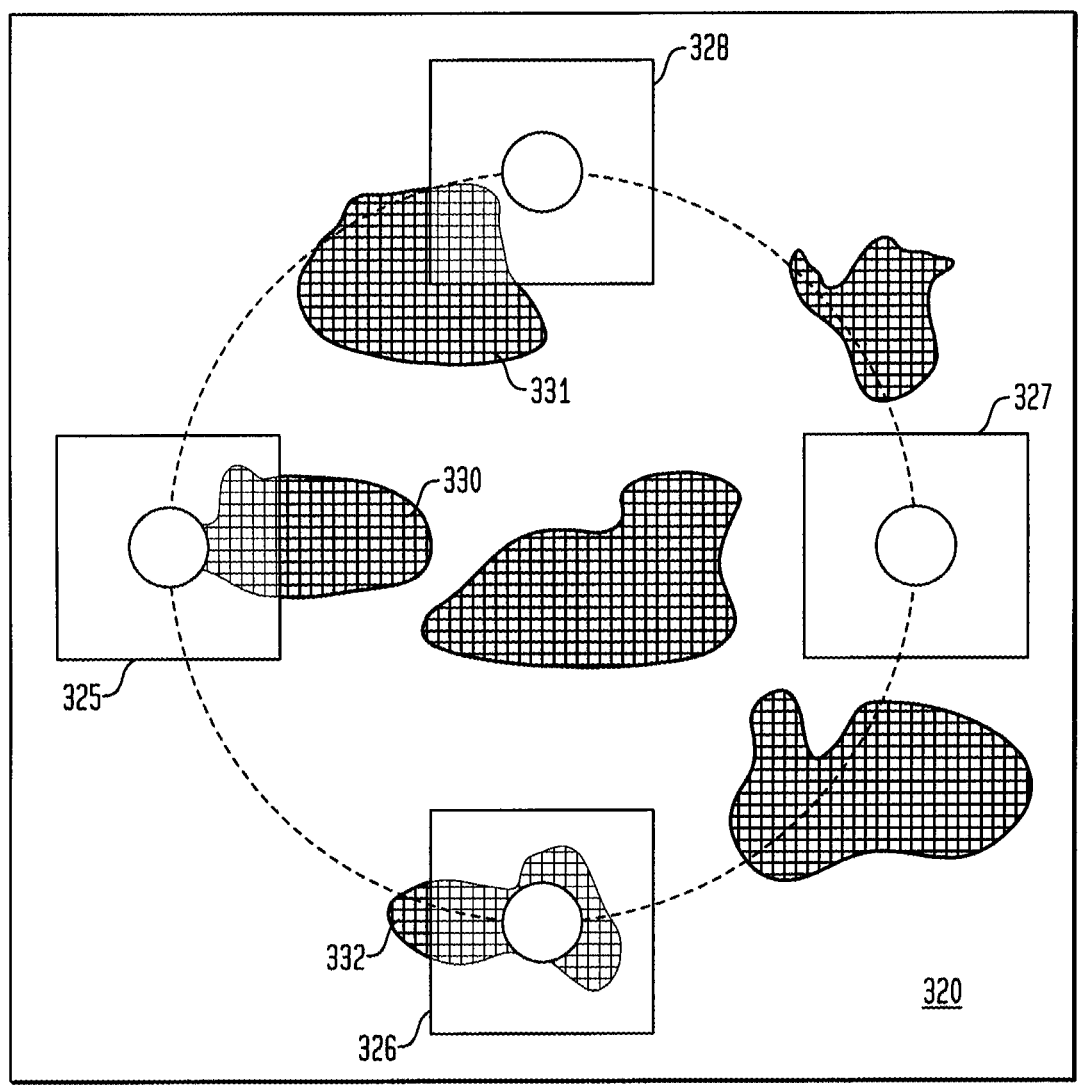
FIG. 3C is a schematic diagram of the tissue site distribution around a circular pattern overlaid with varying analyte correlating regions, according to some embodiments of the present invention.

FIGS. 3A-3C provide some exemplary orientations for tissue sites which can be scanned with an OCT device. As shown in FIG. 3A, a beam scanner can be configured to distribute tissue sites to be scanned around a circular path. The beam scanner can thus move the beam around a diameter 13 to distribute tissue sites therearound. As well, the beam scanner can move an OCT beam within a length scale 23 to provide OCT measurements which can be correlated to an ACR potentially. FIG. 3B presents another pattern of tissue sites that can be scanned with an exemplary beam scanner. The tissue section 310 can be gridded into a set of adjacent sites 311 that substantially cover the tissue section 310. Accordingly, a beam scanner can be configured to move the beam such that tissue sites are distributed over a length scale 14, while each tissue site is interrogated on a smaller length scale 24. It is understood that for any tissue site pattern, the number of tissue sites to be distributed, the shape of the pattern on which tissue sites are distributed, and the scanning within the tissue site can all be varied. For example, the tissue site need not be square shaped, and the entire tissue site need not be interrogated to obtain data for OCT scanning.

FIG. 3C schematically depicts a tissue site 325, 326, 327, 328 distribution pattern to be interrogated by a beam scanner overlaid with the analyte correlating regions 330, 331, 332 of a tissue sample 320. As depicted, some tissue sites 325, 326, 328 intersection portions of ACRs 330, 332, 331, while one tissue site 327 does not interrogate an ACR. Accordingly, by identifying the tissue sites that intersect ACRs, a more targeted analysis and gathering of OCT data can be performed to obtain analyte levels in the tissue 320.

Figure 4:
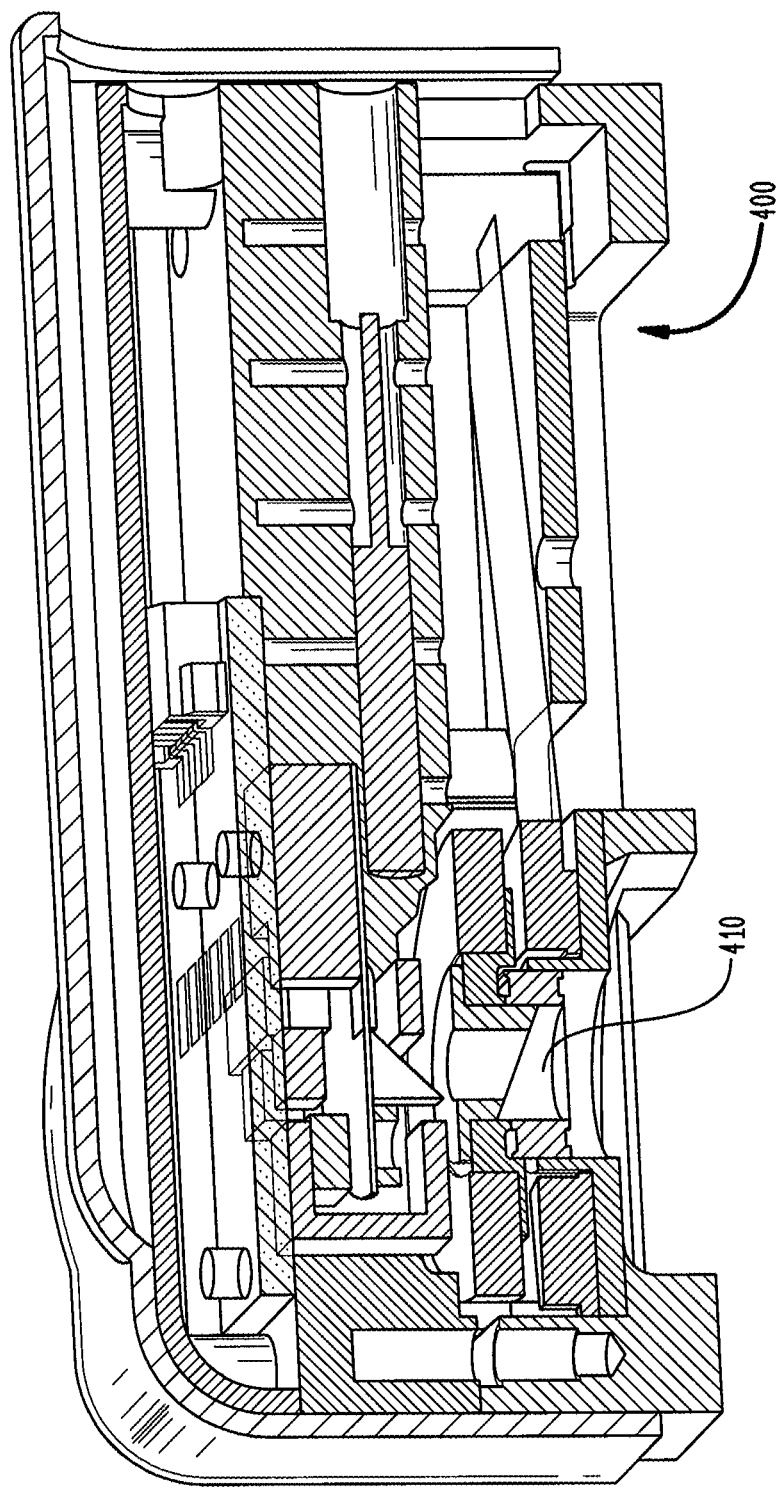
FIG. 4 is a cross-sectional perspective view of a beam scanner with a scanning optic, according to one embodiment of the present invention.
Figure 5:
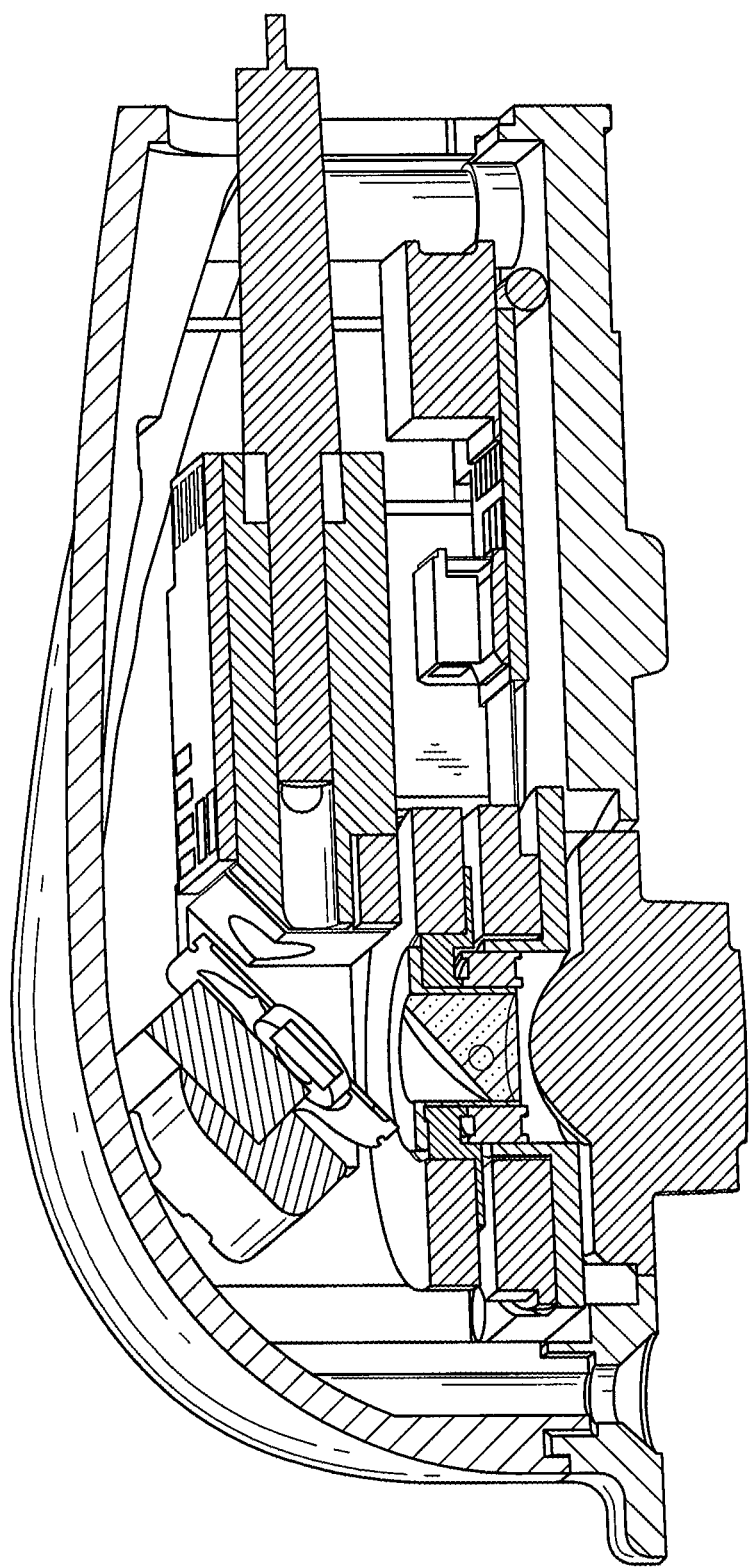
FIG. 5 is a cross-sectional perspective view of a beam scanner with a two scanning optics, according to another embodiment of the present invention.

FIGS. 4 and 5 depict embodiments of beam scanners that have been reduced to practice. FIG. 4 depicts a beam scanner 400 which utilizes two discrete optical elements. One optical element can locate tissue sites by utilizing a rotating wedge prism 410, which can displace the tissue sites around a circle, as depicted in FIGS. 3A and 3C. The other optical element can provide the scanning within a tissue site (e.g., raster scanning). This element can be embodied as a movable mirror, for example a mirror coupled to a flexure. The flexure can be attached to electromagnetic coils to affect its positioning of the mirror, which allows scanning within the tissue site.

FIG. 5 depicts another embodiment of a beam scanner, which utilizes a single optical element for beam steering. The optical element is coupled to a flexure, where the flexure is configured to move the optic (e.g., a mirror) with a greater deflection angle, relative to the flexure used in the device shown in FIG. 4. In this particular flexure, all positions of within a selected spatial extent are scannable, akin to what is shown in FIG. 3B. Accordingly, a greater variation in designation of tissue sites, and scanning within tissue sites, can be achieved with this design. It is understood that other beam scanners can utilize any number of optical elements and/or devices to manipulate the optical elements, in a manner consistent with the functionality of the described devices, including using such elements within the knowledge of one skilled in the art.

Figure 6A:
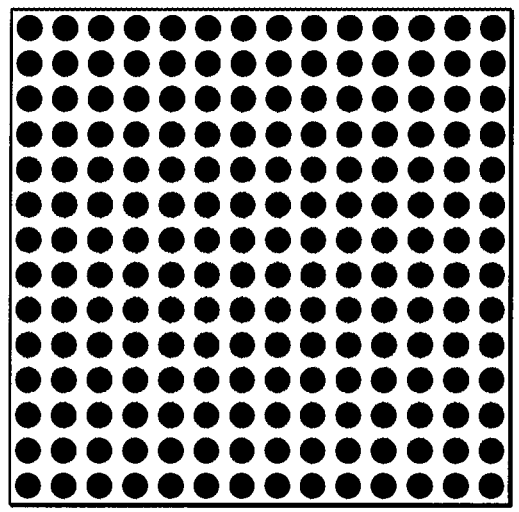
FIG. 6A is a schematic diagram corresponding to locations scanned within a tissue site to substantially scan the tissue site, according to one embodiment of the present invention.
Figure 6B:
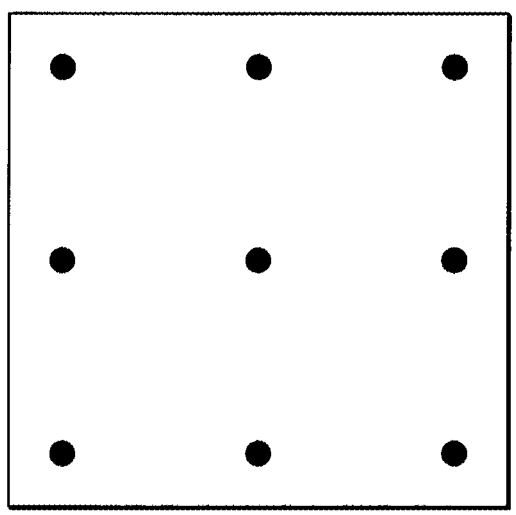
FIG. 6B is a schematic diagram corresponding to locations scanned within a tissue site to scan a plurality of locations in the tissue site, according to another embodiment of the present invention.

With regard to scanning within a tissue site, beam scanners can be configured to perform such scanning using various methodologies. The scanning can be sufficient to substantially cover an entirety of a tissue site as shown in FIG. 6A, or can scan a variety of locations in the tissue site that are spaced apart. For instance, the scanning can be such that enough locations are scanned in a manner to allow reduction of speckle when the OCT measurements are combined to estimate an analyte level. In some embodiments, a raster scan is performed within the tissue site. The raster scanning can be performed in any designated pattern, with as many or few locations actually probed as desired; one example is shown in FIG. 6B. For example, the raster scanning can be of an area, a line, or a volume of locations. In many instances, the raster scanning is done at a plurality of depths of tissue.

As discussed earlier, a controller can be incorporated with an OCT system and/or a beam scanner to aid in the scanner's operation. For example, a controller can be used to associate each of a plurality of tissue sites with particular OCT measurements taken therefrom. The OCT measurements can be used to estimate selected analyte levels therefrom, or can be used to "validate" the site for estimating selected analyte levels (e.g., using the data to determine whether the site covers a sufficient amount of an ACR to extract analyte level data therefrom). In some embodiments, the controller can select the tissue sites (e.g., the validated tissue sites) that will be interrogated in further detail, for instance taking further OCT measurements to determine analyte levels from data taken therefrom. Alternatively, if data for determining analyte levels has been extracted from a set of tissue sites previously, the controller can act to determine which tissue site(s) should be examined to determine analyte levels.

Validation of a tissue site for OCT analyte measurement can be performed using any number of techniques including those known to one skilled in the art for analyzing OCT data. Some embodiments utilize OCT measures of tissue hydration as a technique for validating a tissue site. When an analyte is associated with the level of hydration in a tissue sample (e.g., the amount of blood perfused tissue), one measure of whether the site encompasses an ACR is a measure of the hydration level in the tissue. As discussed in U.S. Pat. No. 7,254,429 and U.S. Patent Application Publication No. U.S. 2006/0276696 A1, a section of tissue can be scanned at two wavelengths, one wavelength that has a low absorption coefficient for water/blood components and a high scattering coefficient for such components (e.g., 1310 nm), and one wavelength that has a high absorption coefficient for the water/blood components (e.g., 1450 nm). By comparing the intensity of backscattered light over a tissue sample at each of these components, one can establish a measure of hydration in the tissue sample. For example, the difference in the average intensity level of OCT backscattering of a tissue site between two wavelengths can be calculated and serve as a validation metric. When the average difference exceeds some threshold value, the site can be designated "valid," while a measure below the threshold value can be designated "not valid." Since the average intensity value depends upon the spatially distributed backscattering intensity, validation of a tissue site can also depend upon the extent to which an ACR overlaps the interrogated tissue site. Referring back to FIG. 3C, a tissue site 327 which does not intersect an ACR will have a low difference value. Tissue sites 325, 326, 328 that intersect an ACR will provide a difference value that depends not only on the analyte level in the ACR but the relative overlap of the ACR with the tissue site. Accordingly, one tissue site 326 can exhibit a higher difference value that other tissue sites 325, 328 that intersect ACRs even if all the ACRs have the same analyte levels therein. Variations on such techniques are also included within the scope of the present application. For example, validation of a tissue site can be performed by examining OCT data taken at two different wavelengths where the wavelengths are selected to provide a contrasting signal indicative of the presence of a particular analyte, for example oxygenated hemoglobin vis-à-vis deoxygenated hemoglobin as discussed in U.S. Patent Application Publication No. U.S. 2005/0059868 A1. It is also understood that combinations of validation techniques can be implemented to provide tissue site validation.

Some embodiments are directed to beam scanners and/or controllers that are configured to validate and/or select a site based upon an OCT measurement indicating the presence of blood flow. The measure of blood flow can be identified in a variety of ways, as described within the present application. Accordingly, embodiments of the invention are directed to devices (e.g., OCT systems, beam scanner, and/or controllers) that are configured to detect fluid flow (e.g., blood flow) using any combination of the techniques discussed herein. Such blood flow can be associated with an analyte, and therefore the validated tissue site with blood flow can be subjected to further OCT measurements and/or data analysis to extract analyte levels.

As previously mentioned, validated tissue site(s) can be interrogated and/or data analyzed therefrom to associate a corresponding analyte level therewith. In some instances, a controller can aggregate the analyte levels from two or more validated sites to provide an aggregated measure of the analyte level in the tissue. Such aggregation can be an average value, a median value, or other aggregated value as understood by one skilled in the art; some further aspects of how aggregation can occur, and thus be implemented in a controller, are discussed herein. Alternatively, or additionally, the analyte levels corresponding with one or more validated sites can be used to calibrate an OCT system such that future OCT measurements utilize the calibration. Such calibration can utilize any of the techniques described in U.S. Patent Application Publication Nos. U.S. 2006/0264719 A1 and U.S. 2006/0276696 A1.

Optic/Skin Contacting Devices

Some embodiments of the present invention are directed to a structure for coupling an optic to a subject, which is configured for use with an OCT measurement. Some exemplary embodiments include the structure itself, an OCT system with such a structure, or a patch. Embodiments can include one or more features as described herein. Such coupling structures can be configured to reduce mechanical distortion of the skin at a measuring site. The distortion includes two types. First, the local distortion of the skin due to the protrusion of the optic surface into the skin. Reducing this effect can hinder longer term stretching and/or the need to accommodate a continuous change in the baseline signal due to the stretching. Such changes, referred to as settling, are not correlated with analyte changes and represent the viscoelastic response of the skin to the pressure of the optic. At the same time, however, protrusion of the optic can be desirable to insure stable continuous contact of the measuring surface with the skin under all conditions of force on the sensor or assembly. The second category of distortion is due to forces on the sensor such as sensor weight, inertia during movement, or brushing the sensor against an object. Also, a sensor cable can transmit some force to the assembly in the form of a torque or a pull, causing motion that deforms the skin macroscopically over the disposable attachment region. Examples are a twisting of the skin that may rearrange the analyte correlating structures in depth, or a pull that due to the varying modulus of the features in the skin causes a change to the baseline interferometer signal.

Figure 7A:
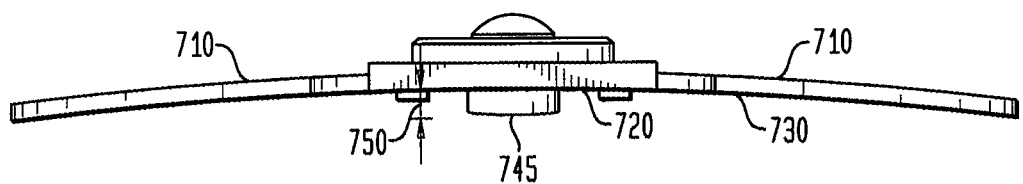
FIG. 7A is a side view of a skin contacting device, consistent with an embodiment of the present invention.
Figure 7B:
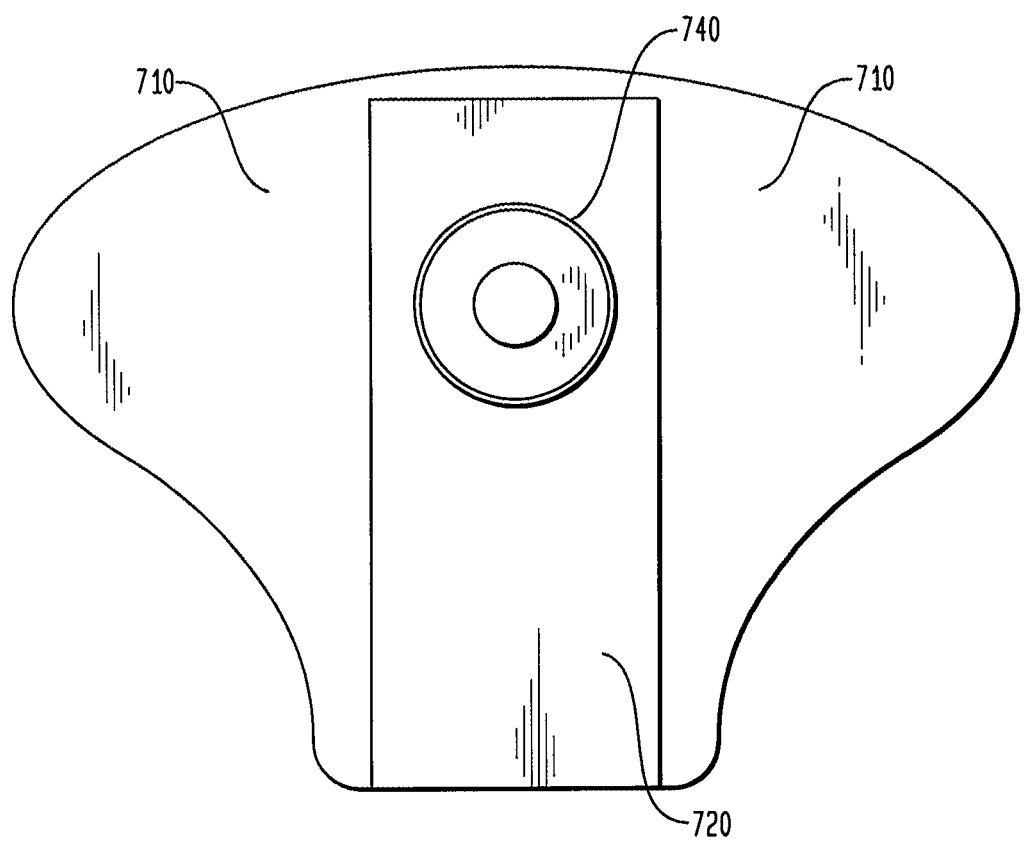
FIG. 7B is a top view of the skin contacting device of FIG. 7A.

Some exemplary embodiments are directed to a structure for coupling an optic to a subject that include one or more optical elements that can be coupled to an OCT system to guide reflect light from skin. One particular embodiment is shown in FIGS. 7A and 7B. An optic 740 can include a protruding portion 745 for contacting the skin of a subject. A patch can be used to align the optical element on the subject's skin. The patch can include a rigid body 720 coupled to the optical element 740 to stabilize the optical path lengths between the element and the skin. The optical element 740 can optionally be removably couplable with the rigid element. Accordingly, in some embodiments, the patch section can be configured as a disposable element, with the optic being reusable. The patch can further include a plurality of pliable extensions 710 coupled to the rigid body 720. Each extension can be configured to extend away from the rigid body, and configured to hinder movement of the rigid body relative to the skin. Extensions can be constructed with any suitable material having a flexible quality; non-limiting examples include polymer-based materials that can optionally have elastic qualities. Adhesive 730 can be applied to couple the structure to the skin. It is understood that the precise configuration of such a structure as shown in FIGS. 7A and 7B does not limit the scope of such structures.

Other embodiments are directed to a optic-skin interface that can help remove moisture from the interface. If moisture from the skin is allowed to build up at the interface, the optical interface to the skin can be distorted and the characteristic shape of the baseline scan can change. Accordingly, one exemplary embodiment is directed to a patch for OCT measurements that includes an optical element and a moisture removing structure 750 as shown in FIG. 7A; it is understood that the moisture removing structure need not be incorporated with all the exact features depicted in FIG. 7A. The moisture removing structure can be configured to transport moisture away from the skin to hinder moisture build up at the interface between the optical element ad the skin. The moisture removing structure can utilize any number of moisture-absorbent materials and/or hydrophilic materials. For example, a hydrophilic foam can be used which allows moisture to be removed by capillary action from the skin and transported to an exterior surface of the foam for evaporation to the external environment. A moisture removing structure can also be embodied as a perforated structure around the optic, which can allow moisture to evaporate directly through the perforations.

It is understood that other features for coupling OCT optics to a subject can also be incorporated within the scope of the present invention. Some of the these features are described in U.S. Patent Application Publication No. U.S. 2007/0219437 A1.

Methods of Estimating Analyte Levels Using OCT

Some embodiments are directed to methods of determining or estimating analyte levels in a tissue using OCT measurements. These methods can be practiced using any number of devices including any appropriate combination of the devices revealed in the present application. However, it is understood that such methods can also be implemented using other devices, including those known to one skilled in the art, albeit specifically configured to practice the embodied method. Accordingly, these methods are not limited by the specific devices, and their delineated operation, revealed elsewhere in the present application. Likewise, the methods described herein, and portions thereof, can be implemented on devices described in the present application. Accordingly, some devices, such as a beam scanner and/or controller, can be configured to carry out portions or the entirety of a method consistent with some embodiments of the present application.

Figure 8:
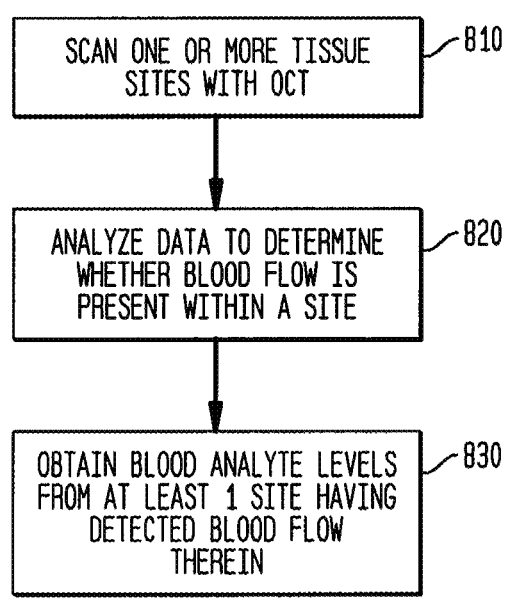
FIG. 8 is a schematic of a flow diagram for detecting blood analyte levels in tissue, according to an embodiment of the present invention.

Some embodiments of methods for estimating analyte levels in tissue are consistent with the flow diagram depicted in FIG. 8. One or more tissue sites can be scanned using OCT 810. Scanning can occur over a two-dimensional region (e.g., at a specified depth), or can be scanning over a volumetric region (e.g., scanning a designated area at a multiplicity of depths). A tissue site can be defined as discussed with respect to beam scanners herein. For example, the tissue site can be spatially distinct from any other (e.g., not overlapping), and/or can be spaced apart from one another. Next, the data collected from the scanning can be analyzed to determine whether blood flow is present in the corresponding tissue site 820. The data can correspond with backscattered light from the OCT measurements, which can potentially carry information about the presence of blood flow. Finally, a measure of a blood analyte level can be obtained from one or more of the tissue sites that exhibits blood flow from the analyzed data 830. Measurement can include the steps of obtaining OCT data from the sites where blood flow is present to obtain data sufficient to estimate an analyte level, and/or analyzing pre-obtained OCT data in a manner to extract analyte levels.

Figure 9:
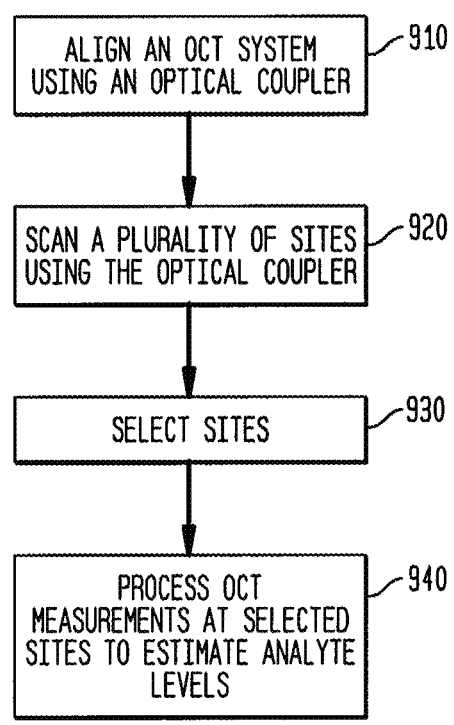
FIG. 9 is a flow diagram of a method for processing OCT measurements, according to an embodiment of the present invention.

Some embodiments of methods for estimating analyte levels in tissue are consistent with the flow diagram depicted in FIG. 9. An OCT system can be aligned using an optical coupler to a subject 910. For instance, a coupling can be attached to a subject through which light is transmitted and reflected to obtain OCT measurements.

A plurality of tissue sites (e.g., at least two) can be scanned using the optical coupler 920. Scanning can occur over a two-dimensional region (e.g., at a specified depth,) or can be scanning over a volumetric region (e.g., scanning a designated area at a multiplicity of depths). The tissue sites can be defined as discussed with respect to beam scanners herein. For example, the tissue sites can be spatially distinct from one another (e.g., not overlapping), or can be spaced apart using some characteristic length scale, as discussed earlier. As discussed earlier, any combination of the OCT measurement techniques discussed by the references disclosed herein, or as utilized by embodiments including a beam scanner as discussed herein, can be utilized to perform the scanning step. In one example, the entirety or portions of a tissue can be scanned as depicted in the selected patterns of FIGS. 3A and 3B, or any other selected pattern. As well, within a tissue site the entirety or a portion of the tissue site can be scanned. In another example, scanning can be performed within a tissue site to provide an OCT measure of an analyte level that is reduced in speckle content and/or is oriented toward a non-imaging technique. Scanning of a tissue site can be performed to render a variety of data types as well. For example, the scanning can provide data that can be converted to an estimate of analyte levels, and/or the scanning can provide data that allows validation of a tissue site as described in the present application.

One or more of the scanned tissue sites can be selected 930 for further processing. Such selection can be performed either after scanning of all tissue sites is completed, or at any time after a particular tissue site has been scanned. In some embodiments, a survey of tissue sites can be initially scanned to determine which will be selected for OCT analyte estimation processing. Alternatively, or in addition, sites can be investigated in an on-going manner (e.g., after a selected number of interrogations for analyte level estimation on a cyclic basis) to continue to validate that the tissue site is appropriate for analyte level estimation. Such on-going selection of tissue sites can act to monitor the potential perturbations and/or physiologic drift that can occur in tissue to alter the location of an ACR. Use of an on-going site selection monitoring technique can result in an adaptive technique that helps maintain the accuracy of an analyte level estimator. In some embodiments, the selection is performed by validating the tissue site using any of the variations discussed within the present application (e.g., using a measure of tissue hydration level, or using a multiple wavelength measuring technique that highlights the presence or absence of a selected analyte).

OCT measurements at the selected tissue sites can be processed to estimate analyte levels 940. For example, processing can include using data at validated sites to calibrate an OCT sensor. Such calibration can be as previously mentioned in the present application. In another example, when more than one site has been selected (e.g., validated) analyte levels corresponding with each of the validated sites can be aggregated to provide an aggregated measure of the analyte level in a tissue. Aggregation can also include aggregating all the data associated with selected tissue sites at once without determining an individual analyte level estimate for each tissue site. Aggregation can be performed in a variety of manners. Some non-limiting examples include: simple or trimmed mean/median of all signals, weighted averaging based on signal properties, weighted averaging based on input from the site selection algorithm, or some kind of cross-correlation/convolution of the signals.

Figure 10:
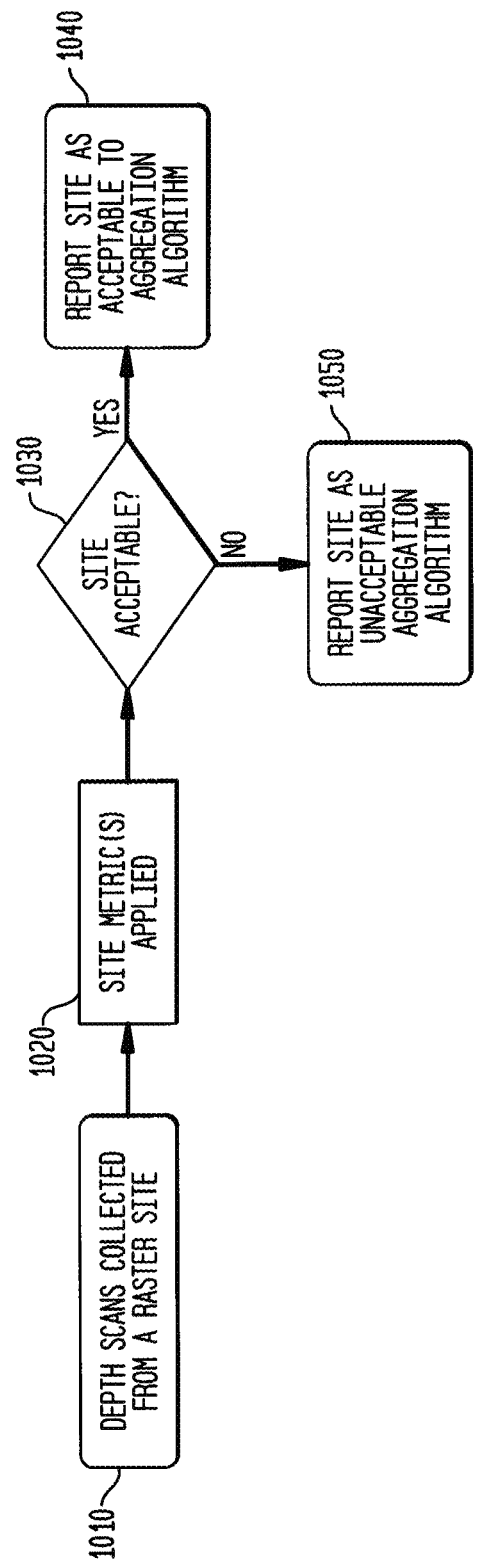
FIG. 10 is a flow diagram of a method for determining whether a site is valid, consistent with one embodiment of the present invention.

FIG. 10 provides one example of a method for performing site selection. Scans (e.g., depth scans) are performed for a number of tissue sites, with depths being probed by a raster scan 1010. Next, site metrics are applied 1020 to determine if a site is acceptable. Such site metrics can include site validation determination using OCT scans at different wavelengths of light to characterize tissue. If a site is acceptable 1030, 1040, its OCT measurements can be used to identify an analyte level, such as by using its measurements in an aggregation algorithm with other acceptable site data. If the site is not validated 1030, 1050 it can be considered unacceptable for measuring analyte levels. It is understood that site that are designated unacceptable may be acceptable at later times, for example when implementing an on-going validation site methodology.

Figure 11:
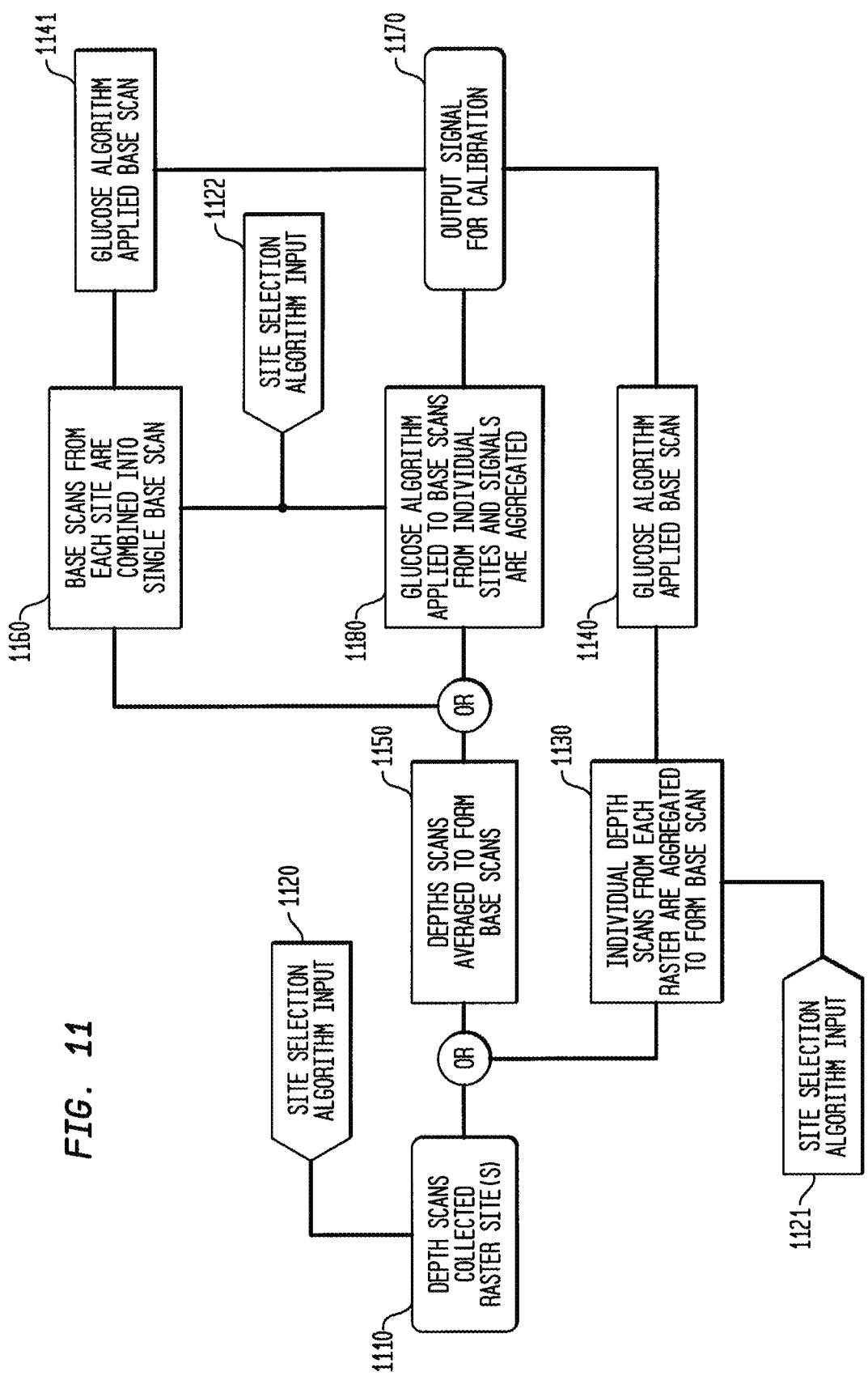
FIG. 11 is a flow diagram showing a variety of techniques for aggregating OCT data measurements, according to one embodiment of the present invention.

Aggregation can take place at several points in the data process as exemplified in the flow diagram of FIG. 11: First, depth scans can be collected 1110 from raster scanning a number of tissue sites. In one instance, the individual depth scans can be validated using a site selection algorithm 1120, 1121, 1122 with the selected sites being aggregate to form a base scan 1130. An analyte converting technique (e.g., glucose conversion technique 1140) can be applied to the aggregated base scan to form an analyte level measure, which can subsequently be used to calibrate an OCT system 1170. In another instance, the individual depth scans can be averaged to form corresponding base scans 1150. The base scans can each be subjected to a site selection algorithm 1121 to determine which are valid. The valid scans can then be further analyzed to report analyte levels for calibration of an OCT system. The analyte levels for corresponding to each valid site can be aggregated 1180, or the OCT data of the valid sites can first be combined into a single scan 1160 before the analyte level is determined for the base scan.

Fluid flow detection using OCT can be achieved using a variety of methodologies. One methodology involves detecting changes in a speckle pattern indicative of the presence of fluid flow. In many instances, each raw OCT scan can exhibit a high degree of speckle in the signal due to the micro-roughness of the skin and the coherence of the optical source. Some aspects of this effect are described in U.S. Pat. No. 7,254,429. This speckle "noise" on the underlying depth intensity signal is a function of the optical coherence length, wavelength, distance from the focal point, size and shape of the scattering centers, and optical properties of the scatterers and the surrounding media. In speckle flowometry, the particles in the flowing fluid (e.g., red blood cells in blood) can cause the speckle pattern in the region of the flow to change in time more rapidly relative to the change in the speckle of the surrounding tissue. Tissue sites with a high degree of speckle temporal variations are sites where blood flow exists. Thus, when an blood analyte (e.g., blood glucose) is sought to be identified, the presence of blood flow can correspond with the presence of an ACR.

Accordingly, some embodiments are directed to techniques that utilize OCT intensity data measurements that exhibit speckle. The speckle in these measurements can be analyzed to determine whether blood flow is present, for example by comparing two or more different intensity data measurements. Comparison of intensity data measurements for speckle differences can occur in a number of ways. In one instance, two or more scans at one location at a particular tissue depth are repeated at different moments in time (e.g., over a time period of less than about a few seconds). Comparison of the corresponding intensity data sets can indicate the presence of fluid flow if the changes in speckle are substantial. If this is also performed at varying depths, providing intensity data sets of a set of locations at different times and depths, comparison of the intensity sets can also indicate where blood flow is more of less prevalent depending upon the relative temporal changes in the speckle pattern as different times (e.g., more change corresponding with more flow). It is understood that more than one location could potentially be scanned, with the trade-off of requiring more time to complete which can complicate a temporal analysis.

In another instance, a set of scans (e.g., raster scans) is performed at a variety of locations (e.g., linear raster scans) at varying depths. The depths that are more similar to one another in speckle pattern can be indicative of less blood perfused tissue, while depths that differ in speckle pattern can be more indicative of the presence of blood perfused tissue. This technique can potentially require less data than the formerly described technique, but with a trade off of signal to noise ratio.

Another methodology for detecting fluid flow using OCT relies on techniques associated with Doppler OCT, or more particularly in examining the frequency modulation in an OCT fringe signal due to the interaction with fluid flow. As mentioned earlier, when the phase shifter in a reference arm of an OCT system moves at a constant velocity, a corresponding fringe frequency is established. In fringe frequency modulation, moving particles in a flowing fluid can cause a shift in the observed frequency of the interferogram in the region of the blood flow. Accordingly, this technique utilizes some principles like what is exploited in ultrasonic imaging of blood flow. Previous work in Doppler flowometry has adopted this technique for OCT, and relies on analyzing the shift in the peak frequency. Examples of such work include Zvyagin, et al., "Real-time detection technique for Doppler optical coherence tomography," Optics Letters, Vol. 25, No. 22, Nov. 15, 2000, pp. 1645-47; Davé et al., "Doppler-angle measurement in highly scattering media," Optics Letters, Vol. 25, No. 20, Oct. 15, 2000, pp. 1523-25; Zhao et al., "Doppler standard deviation imaging for clinical monitoring of in vivo human skin blood flow," Optics Letters, Vol. 25, No. 18, Sep. 15, 2000, pp. 1358-60; Zhao et al., "Real-time phase-resolved functional optical coherence tomography by use of optical Hilbert transformation," Optics Letters, Vol. 27, No. 2, Jan. 15, 2002, pp. 98-100; Barton et al., "Flow measurement without phase information in optical coherence tomography images," Optics Express, Vol. 13, No. 14, Jul. 11, 2005, pp. 5234-39. Doppler flowometry can be very sensitive to orientation of the flow relative to the incoming beam from the OCT sensor which provides a challenge in extracting quantitative blood flow measurements.

Accordingly, some embodiments are directed to techniques for detecting fluid flow (e.g., blood flow) by scanning one or more tissue sites to collect fringe modulated data and analyzing the fringe modulated data for the presence of blood flow in the tissue site. Such measurements can be made at varying depths, which can allow the fringe frequency to be determined.

Determination of the presence of fluid flow can be achieved in a variety of manners. A shift in fringe frequency components (e.g., shift in the peak fringe frequency) relative to what is expected from a moving phase shifter can indicate the presence of fluid flow. Using other techniques known to those skilled in the art, further data can be extracted including directionality of the scatterers and a velocity profile. Such detailed information, however, can require substantial data processing. Accordingly, some embodiments utilize a digital signal processing to extract the shift in a peak frequency. For example, when a phase shifter is configured to provide a 600 kHz baseline signal, oversampling by a factor of 5 or more will typically utilize a 3 Msps system with at least 12 bits of data conversion resolution.

Some embodiments are directed to techniques that examine the amplitude modulation of an OCT signal (e.g., vis-à-vis a tissue sample with no fluid flow) to determine if fluid flow is present. Amplitude modulation is distinct from looking at the shift in the peak fringe frequency, and can include such observables as the examining the intensity changes at selected frequencies, the frequency broadening, and/or a shape change in a fringe-frequency envelope. For instance, the backscattered OCT signal can be examined for a change in total intensity of the signal (e.g., over a given bandwidth), and/or a measure of the broadening of the fringe-frequency envelope relative to the initial OCT signal. As an OCT beam interacts with moving particles, not only does the main frequency shift due to the movement but the breadth of the frequency components can also grow. Without necessarily being bound by any particular theory, it is believed that speckle plays a role in frequency broadening. Since speckle has a tendency to create high frequency components in the data, such components are more likely to be shifted by interaction with scatterers. Accordingly, detection of the amplitude modulation of the envelope of frequencies can be an indicator of the presence of fluid flow. For example, digital signal processing can be applied to a backscattered signal to create a measure of the amplitude modulation (e.g., looking at a measure of the shape change in the envelope relative to what is expected for tissue without fluid flow or relative to an initial signal).

In some embodiments, examination of the amplitude modulation can also allow the use of less data intensive techniques for signal processing relative to known techniques that follow the Doppler shift in a peak frequency. If properties such as directionality and relative velocity are not to be determined, simpler signal processing techniques (e.g., analog signal processing) can be utilized, though more advanced data processing is not precluded. For instance, the integrated power of an interferogram can be examined to determine the presence of fluid flow. Thus, detection of the envelop shape of a return signal, relative to an expected shape, can be enough to determine the presence of fluid flow. Thus even though directionality information is lost, an indication of fluid flow is more easily identified with less data processing. It is understood, however, that techniques susceptible to use with analog signal processing can also substitute digital signal processing, consistent with some embodiments of the present invention.

For instance, in some embodiments, a backscattered wide band signal from an OCT system is filtered to determine the presence of fluid flow. The filtered signal of a backscattered wide band signal can be used, in some embodiments, to produce a filtered signal indicating fringe frequency modulation indicative of blood flow's presence. Such a system can utilize either analog or digital signal filtering. One filter applied to the backscattered signal can be a narrow band filter, which can be centered at the base fringe frequency set by the phase shifter. The width of the filter frequencies can be chosen such that the filtered backscattered signal is indicative of the presences of fluid flow. For example, the filtered backscattered signal from tissue with little to no fluid flow has substantially higher intensity than the filtered backscattered signal from tissue with fluid flow present. Accordingly, in some situations, the bandwidth of the narrow band filter can act to reduce the intensity of a backscattered OCT signal by eliminating higher and lower frequency components that shift out of the bandwidth due to the presence of fluid flow.

Another filter can also be applied to the raw backscattered OCT signal, where this filter is a wide band filter, relative to the narrow band filter, which can also be centered at the base fringe frequency set by the phase shifter. The wide band filter can be configured with a bandwidth such that a portion of backscattered OCT signal, when scattering is from tissue having fluid flow present, is still in the filtered signal (e.g., at least one fringe-modulated feature). Accordingly, comparing the intensity data from the wideband filter output and the narrow band filter output can be indicative of the presence of fluid flow. In particular, the use of the wide band filter can act to allow adjustments due to tissue movement or other changes not due to detecting fluid flow, thus decreasing the possibility of false positives.

It is understood that digital or analog filters for amplitude modulation examination can have a number of other configurations that differ from what has just been described. For example, a filter need not be symmetric about a centered frequency, and/or the filter need not be centered at the frequency of the initial fringe-frequency. Indeed, the filter(s)

can be chosen in any suitable manner to accentuate identification of amplitude modulation to aid fluid flow determination.

Figure 12:
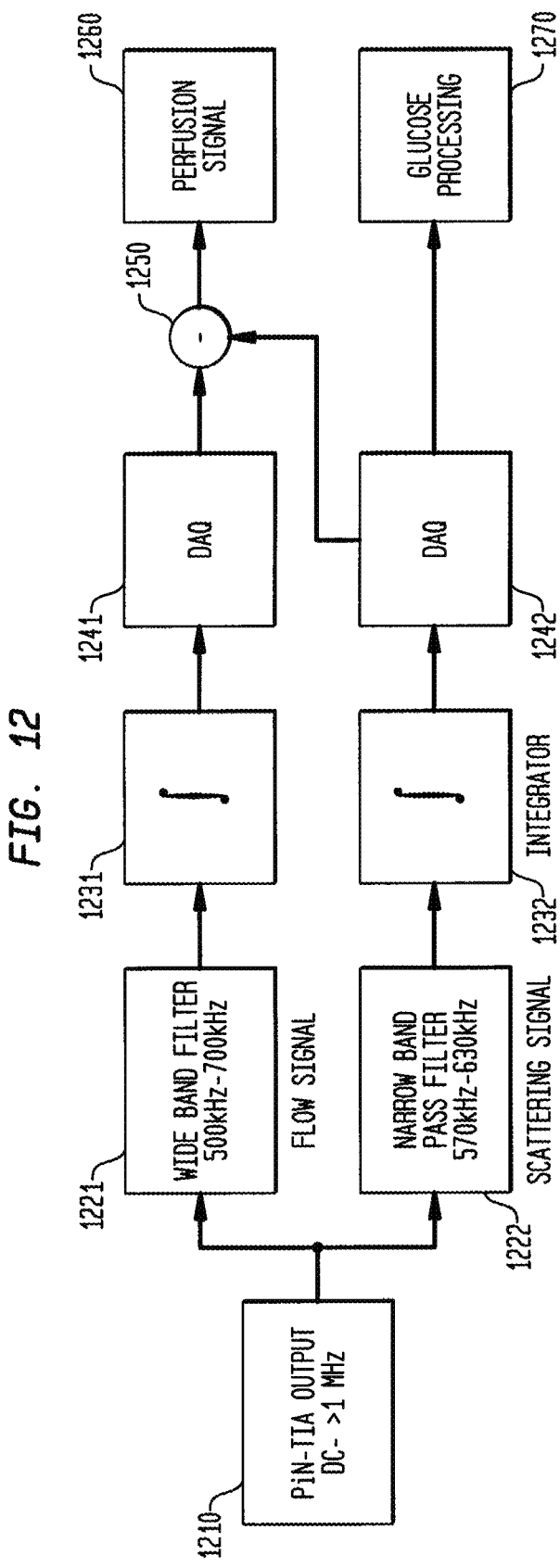
FIG. 12 is a schematic flow diagram of a multi-filtering method for detecting fluid flow, according to an embodiment of the present invention.

One exemplary embodiment of the use of a multifiltered backscattered OCT signal system for fluid flow detection is shown in FIG. 12. A backscattered signal can be received from reflected light from the tissue of a subject interrogated using an OCT system. The OCT system can utilize a base phase fringe signal having a frequency of around 600 kHz centered. The wide band output of an optical receiver 1210 that accepts the reflected light can be routed through at least two filter channels. The narrowband channel contains a narrow band pass filter 1222, centered on the original fringe rate of the interferometer. The filtered signal is then integrated 1232 and passed through a data acquisition board (DAQ) 1242 to be further processed by a computer 1270 (e.g., for obtaining glucose level estimations). The narrow filter signal can be used to compute structural changes induced by glucose variations. As a side effect, this filter 1222 will reduce the contribution of scattering by blood and blood related components as Doppler induced shift from the blood flow will move the signal outside of the filter band pass.

The wideband channel of FIG. 12 passes the backscattered OCT signal through a wide band pass filter 1221 which is also centered at the original fringe rate of the interferometer. The wide band filtered signal is also integrated 1231 and then digitized by the DAQ 1241. The wideband channel contains higher or lower additional frequency components of the signal. Due to the Doppler shift and spectral broadening generated by the passing blood cells, the wide band signal will increase relative to the narrow band one whenever flowing blood is encountered. Differences between these narrow band and wide band signals, as determined by a comparator 1250 for example, can then be used as indicators of the depth and magnitude of blood flow. An indication of the blood perfusion in the scanned tissue 1260 can then be provided. While the directional information is lost with this technique, the simplicity of implementation, and the natural conversion speed of analog processing make such an embodiment potentially useful.

As mentioned earlier, the use of amplitude modulation in an OCT signal to detect fluid flow can also utilize analysis of the speckle in the backscattered OCT signal. For instance, the multi filter approach described above can also be applied to the speckle analysis. Since a narrow band filter can be configured to reduce the intensity of the observed speckle due to fringe frequency shifting, the variance of the speckle can also be lower. Thus, the speckle variance of the resulting OCT signals from the two filters can be compared to identify a difference in the speckle variance in space, in time, or both.

OCT identification of blood flow in a tissue can be used in a number of ways. As alluded to earlier, blood flow identification can provide a measure of blood perfusion in tissue, which can identify whether a tissue section exhibits characteristics for analyte level estimation (e.g., identifying that the tissue has an ACR at a particular set of locations such as at particular depths or lateral extents). The blood flow identification can also serve as an indicator of heart rate by choosing an blood flow location and monitoring the signal's sinusoidal behavior, correlating the oscillatory behavior with heart rate. In some embodiments, during an analyte monitoring session, these blood flow identification techniques can also provide a timely indication of significant sensor disturbance (i.e., the loss of a signal indicating the presence of blood flow), which otherwise may render the analyte measurement inaccurate.

Example Embodiments

The following example is provided to illustrate some embodiments of the invention. The example is not intended to limit the scope of any particular embodiment(s) utilized.

An OCT system was implemented to carry out the method diagrammed in FIG. 12 using commercially available equipment.

A test is carried out at a specific tissue site. An initial OCT scan of the tissue at varying depths is performed. The data over each depth is averaged to give an averaged intensity data at that point. Subsequently, OCT scans of the same tissue site are performed at varying moments in time, each of which is designated by a scan number in FIG. 13. The averaged value of the OCT scan versus depth for each time was subtracted from the initial OCT averaged scan value versus depth. The differences are plotted in the pixel plot shown in the top portion of FIG. 13, where a measure of the difference is provided by the shading of the pixel. The lower portion of FIG. 13 provides a corresponding time graph of measured glucose values in the blood stream of the subject whose tissue was scanned. Accordingly, the comparison of the two plots shows that the OCT method can identify regions of tissue that are susceptible to change due to glucose and the presence of blood flow.

FIG. 14 aggregates the pixel data of FIG. 13 by summing all the difference data at a given depth location over all times. That summation is plotted as a function of depth to provide an indicator of the glucose signal, which is the thick line shown in FIG. 14. The data is normalized on the maximum summation in the data set. The thin line corresponds to a perfusion signal measure obtained using the signal processing exemplified in FIG. 12. The backscattered data from a scanned tissue sample at a given depth was sent through a wide band filter and a narrow band filter. An integrator aggregated the data. The differences between the filter outputs at varying depths was plotted as shown by the thin line of FIG. 14. Again, the data is normalized on the maximum difference value. The correspondence between the lines as a function of time shows that a measure of tissue perfusion can act to identify glucose distortion regions, and can provide a glucose independent site metric.

FIG. 15 is a trace showing the pulsatile blood flow indicative of heart rate that is derived from the OCT data. In particular, the perfusion signal of a well-perfused tissue site is aggregated and followed as a function of time. Since the blood flow rate changes through a cycle of a heart beat, the perfusion signal provides a corresponding change, which is shown in FIG. 14. Accordingly, the heart rate of a subject can be followed.

It is understood that a number of variations on the methods described herein are possible, including variations within the knowledge of one skilled in the art. Indeed, numerous other steps can be added, or particular step omitted (e.g., omitting the aligning step; or simply performing the site selection step on existing OCT data). Such variations are within the scope of the present invention.

Additional Embodiments

While the present invention has been described in terms of specific methods, structures, and devices it is understood that variations and modifications will occur to those skilled in the art upon consideration of the present invention. For example, the methods and compositions discussed herein can be utilized beyond the preparation of metallic surfaces for implants in some embodiments. As well, the features illustrated or described in connection with one embodiment can be combined with the features of other embodiments. Such modifications and variations are intended to be included within the scope of the present invention. Those skilled in the art will appreciate, or be able to ascertain using no more than routine experimentation, further features and advantages of the invention based on the above-described embodiments. Accordingly, the invention is not to be limited by what has been explicitly shown and described.

All publications and references are herein expressly incorporated by reference in their entirety. The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A system comprising:
   a processor configured to:
      receive, from an optical coherence tomography apparatus, an intensity data measurement for a region of tissue;
      pass the intensity data measurement through a first frequency band filter having a first bandwidth to produce a first output;
      pass the intensity data measurement through a second frequency band filter having a second bandwidth that is wider than the first bandwidth to produce a second output; and
      determine an indication of fluid flow in the region of tissue by comparing the first output and the second output.

2. The system of claim 1, wherein both the first bandwidth and the second bandwidth are centered at a same base frequency.

3. The system of claim 1, wherein the processor is further configured to:
   in response to determining a positive indication of fluid flow in the region of tissue, determine a blood analyte measurement based on at least some of the intensity data measurement.

4. The system of claim 3, wherein the blood analyte measurement comprises a measurement of at least one of: blood glucose, blood hemoglobin, or blood oxygen.

5. The system of claim 1, wherein determining the indication of fluid flow in the region of tissue comprises:
   analyze fringe frequency data in the first output and the second output.

6. The system of claim 5, wherein analyzing fringe frequency data comprises:
   analyze frequency modulation in the fringe frequency data in the first output and the second output.

7. The system of claim 5, wherein analyzing fringe frequency data comprises:
   analyze amplitude modulation in the fringe frequency data in the first output and the second output.

8. The system of claim 7, wherein analyzing fringe frequency data further comprises:
   compare speckle intensity in the first output and the second output.

9. The system of claim 1, wherein determining the indication of fluid flow in the region of tissue comprises:
   compare speckle intensity in the first output and the second output.

10. The system of claim 1, wherein the intensity data measurement comprises a backscattered wide band signal.

11. A system comprising:
    a processor configured to:
       receive, from an optical coherence tomography apparatus, an intensity data measurement for a region of tissue;
       pass the intensity data measurement through a first filter to produce a first output;
       pass the intensity data measurement through a second filter to produce a second output; and
       analyze fringe frequency data of the first output and the second output to determine an indication of fluid flow in the region of tissue.

12. The system of claim 11, wherein the processor is further configured to:
    in response to determining a positive indication of fluid flow in the region of tissue, analyze the intensity data measurement to determine a blood analyte measurement.

13. The system of claim 12, wherein the processor is further configured to:
    analyze a plurality of intensity data measurements for a same region of tissue to determine the blood analyte measurement.

14. The system of claim 13, wherein the plurality of intensity data measurements are obtained at a plurality of depths in the same region of tissue.

15. The system of claim 13, wherein the plurality of intensity data measurements are obtained at a plurality of times for the same region of tissue.

16. The system of claim 12, wherein the blood analyte measurement comprises a measurement of at least one of: blood glucose, blood hemoglobin, or blood oxygen.

17. The system of claim 11, wherein analyzing fringe frequency data comprises:
    analyze frequency modulation in the fringe frequency data in the first output and the second output.

18. The system of claim 11, wherein analyzing fringe frequency data comprises:
    analyze amplitude modulation in the fringe frequency data in the first output and the second output.

19. The system of claim 18, wherein analyzing fringe frequency data further comprises:
    compare speckle intensity in the first output and the second output.

20. The system of claim 19, wherein determining the indication of fluid flow in the region of tissue comprises:
    compare speckle intensity in the first output and the second output.

* * * * *